(12) United States Patent
Voskoboynikov et al.

(10) Patent No.: US 10,159,775 B2
(45) Date of Patent: Dec. 25, 2018

(54) PUMP PRELOAD INDEX/INDICATOR

(71) Applicant: HeartWare, Inc., Miami Lakes, FL (US)

(72) Inventors: Neil Voskoboynikov, Pembroke Pines, FL (US); Pedro Grave De Peralta, Miami, FL (US)

(73) Assignee: HeartWare, Inc., Miami Lakes, FL (US)

(*) Notice: Subject to any disclaimer, the term of this patent is extended or adjusted under 35 U.S.C. 154(b) by 76 days.

(21) Appl. No.: 15/424,057

(22) Filed: Feb. 3, 2017

(65) Prior Publication Data

US 2017/0224895 A1    Aug. 10, 2017

Related U.S. Application Data

(60) Provisional application No. 62/291,123, filed on Feb. 4, 2016.

(51) Int. Cl.
   *A61M 1/12* (2006.01)
(52) U.S. Cl.
   CPC .................................. *A61M 1/122* (2014.02)
(58) Field of Classification Search
   None
   See application file for complete search history.

(56) References Cited

U.S. PATENT DOCUMENTS

| | | | |
|---|---|---|---|
| 7,972,122 B2 | 7/2011 | LaRose et al. | |
| 8,007,254 B2 | 8/2011 | LaRose et al. | |
| 8,419,609 B2 | 4/2013 | Shambaugh, Jr. et al. | |
| 8,512,013 B2 | 8/2013 | LaRose et al. | |
| 2010/0160801 A1* | 6/2010 | Takatani | A61B 5/0215 600/508 |
| 2012/0245681 A1 | 9/2012 | Casas et al. | |
| 2014/0100413 A1 | 4/2014 | Casas et al. | |
| 2014/0357937 A1 | 12/2014 | Reyes et al. | |

(Continued)

FOREIGN PATENT DOCUMENTS

EP    2145638 A1    1/2010

OTHER PUBLICATIONS

K. Takahashi, et al: "Estimation of Left Ventricular Recovery Level Based on the Motor Current Waveform Analysis on Circulatory Support with Centrifugal Blood Pump", Artificial Organs, vol. 25, No. 9, Sep. 1, 2001, 713-718, Blackwell Science, Inc.

(Continued)

*Primary Examiner* — Ankit D Tejani
(74) *Attorney, Agent, or Firm* — Christopher & Weisberg, P.A.

(57) ABSTRACT

A method of estimating an amount of work available to be performed by a blood pump implanted in a patient includes calculating a first coordinate value characterizing a volume of blood impelled in the pump and a second coordinate value characterizing a differential pressure across the pump for each of a plurality of flow rate data points of a given cardiac cycle of the patient, each flow rate data point indicative of a flow rate of blood through the pump. An area enclosed by the first and second coordinate values of the plurality of flow rate data points is determined, the determined area being indicative of an amount of work available to be performed by the blood pump.

8 Claims, 20 Drawing Sheets

(56) References Cited

U.S. PATENT DOCUMENTS

2015/0025328 A1 1/2015 Khair
2016/0166211 A1 6/2016 Brown et al.

OTHER PUBLICATIONS

D. Burkhoff, "Pressure-Volume Loops in Clinical Research, A Contemporary View", Journal of the American College of Cardiology, vol. 62, No. 13, Sep. 24, 2013: 1173-1176.
International Search Report and Written Opinion dated May 8, 2017, for corresponding International Application No. PCT/US2017/016495; International Filing Date: Feb. 3, 2017 consisting of 14-pages.
Pressure-volume loop analysis in cardiology, https://en.wikipedia.org/wiki/Pressure-volume_loop_analysis_in_cardiology.

\* cited by examiner

12:42:57.0 PM

PUMP PRELOAD INDEX/INDICATOR

CROSS-REFERENCE TO RELATED APPLICATION

This application is related to and claims priority to U.S. Provisional Patent Application Ser. No. 62/291,123, filed Feb. 4, 2016, entitled PUMP CAPACITY WORK INDEX, the entirety of which is incorporated herein by reference.

STATEMENT REGARDING FEDERALLY SPONSORED RESEARCH OR DEVELOPMENT n/a

TECHNICAL FIELD

The present invention relates to methods and devices for estimating an amount of work being performed by the heart of a patient when the heart is operating in parallel with an implantable blood pump, and/or an amount of work available to be performed by the implantable blood pump operating in parallel with the heart.

BACKGROUND

An implantable blood pump used as a mechanical circulatory support device or "MCSD" includes a pumping mechanism to move blood. The pumping mechanism may be a radial flow pump, such as the HVAD® Pump manufactured by HeartWare Inc. in Miami Lakes, Fla., USA. The HVAD® Pump is further discussed in U.S. Pat. No. 8,512,013, the disclosure of which is hereby incorporated herein in its entirety. Alternatively, the pumping mechanism may be an axial flow pump, such as the MVAD® Pump, also manufactured by HeartWare Inc., and the pumps described in U.S. Pat. Nos. 7,972,122, 8,007,254 and 8,419,609, the disclosures of which are also hereby incorporated herein in their entirety, or any other pump suitable for providing vascular assistance. In operation, the blood pump draws blood from a source such as the right ventricle, left ventricle, right atrium, or left atrium of a patient's heart and propels the blood into an artery such as the patient's ascending aorta or peripheral artery. Due to the nature of the application, the pumping mechanism must be highly reliable. Patient comfort is also a significant consideration. In addition to the pumping mechanism, the device may include a controller and the drive electronics for the pumping mechanism. The controller and drive electronics may receive power from an external power source. That power may be used to drive a motor of the pumping mechanism at a desired speed.

In some cases, the blood pump may provide only partial support to the patient. In such cases, the patient's heart continues to pump blood from the left ventricle to the aorta through the aortic valve (or, in the case of the right ventricle, to the pulmonary artery through the pulmonic valve), and the blood pump further assists the activity of the patient's heart in parallel. Although the heart only pumps blood into the aorta during systole, the blood pump works during both systole and diastole, when the aortic valve is open or closed. Thus, over a given period of time including systole and diastole, the patient's heart and the blood pump may each be responsible for some of the work performed to pump blood to the patient's arteries.

It is generally understood that increasing the speed of the blood pump causes the pump to perform more work. In some cases, increasing the speed of the pump may be beneficial for the patient, by allowing the pump to perform additional work in tandem with the heart. However, in other cases, the pump may already be operating at a speed at which there is little or no additional work to be performed (e.g., blood to be pumped from the ventricle), in which case increasing patient's heart may simply cause the patient's heart to perform less work, but not necessarily increase the overall work performed. In some cases, increasing motor speed of the blood pump may leave so little work for the heart that the aortic valve is not forced open during systole, thereby transitioning the pump from a state of partial-assistance to a state of full-assistance. Such changes in work performed by the heart may be unwanted. Therefore, it is desirable to determine how much work is being performed by each of the heart and the blood pump, so that it may further be determined whether it is desirable to increase a motor speed of the pump.

Conventionally, the amount of work performed by the each of the patient's heart and the blood pump may be determined based on invasive measurements. For example, ventricular work could be assessed using catheter-based measurements. The catheter-based measurements could be used to construct a pressure-volume loop ("PV loop") indicating the total work performed by the patient's heart. FIG. 1 is a diagram of an example PV loop, showing the volume of blood stored in the patient's left ventricle ("LVV" horizontal axis, measured in microliters) and the pressure exerted by the left ventricle ("LVP" vertical axis, measured in mmHg) over the course of a single cardiac cycle. In the example of FIG. 1, stroke work ("SW") exemplifies the amount of work performed by the heart. The potential energy ("PE") may be considered an indication of the amount of work not performed by the heart, and therefore remaining for the pump to perform.

The above example demonstrates catheter-based measurements for the "left" half of the heart. Similar measurements may be taken for the "right" half of the heart (e.g., right ventricular volume, right ventricular pressure, pulmonary pressure, etc.).

Invasive measurements may also be used to detect a situation in which the blood pump transitions from a state of partial-assistance to a state of full-assistance. For example, catheter-based measurements of left ventricular pressure ("LVP") and aortic pressure ("AOP") may be used to identify aortic valve closure during systole. If LVP and AOP measurements cross over one another during the course of the patient's cardiac cycle (particularly during the transitions between systole and diastole), the cross over is an indication that the aortic valve has opened, thereby causing AOP and LVP to be relatively the same (as compared to during diastole). By contrast, if LVP and AOP do not cross over, that is an indication that the aortic valve has not opened even during systole, since LVP remains below AOP. However, it is impractical to monitor the patient's heart and pump function invasively after the blood pump has already been implanted, particularly while the patient is outside of a clinic or hospital.

SUMMARY

The present disclosure provides systems and methods for determining an amount of work being performed by a blood pump, and more particularly an amount of additional work available for a blood pump to perform. The systems and methods described herein are beneficial for partial assistance blood pumps, in which the blood pump is only partially responsible for pumping blood to the patient's arteries, thereby providing assistance to the work being performed by the patient's heart, as well as for full assistance blood pumps, in which all blood pumped from a given ventricle to its corresponding arteries travels through the pump.

Work may be characterized as an amount of force applied to an object (in this case blood) to move that object a given distance. Since the pressure exerted by the heart is equivalent to the force over the cross-sectional area that the force is applied, the work performed (or to be performed) by the heart may be characterized as the pressure exerted by the heart on the blood multiplied by the cross-sectional area that the pressure is exerted, further multiplied by the distance that the blood is pushed.

Aside from the work performed by the heart, the work not performed by the heart (and thereby left available to be performed by a pump connected thereto) may be similarly characterized. In the case of such work, the work may be thought of as a pressure component of the pump (e.g., differential pressure across the pump) multiplied by a volume component (e.g., a flow rate of blood flowing through the pump, a derivative thereof, etc.).

Available pump work may be estimated, calculated or otherwise determined over the course of one or more cardiac cycles of the patient. Notably, over the course of a cardiac cycle, the pressure and/or volume component of the pump does not necessarily remain constant. Therefore, in such circumstances, the pump work determination should take into account the changes in the pressure and volume components. The present disclosure further provides ways for these changes in the pressure and volume components to be tracked and further integrated into a determination of overall available pump work.

Since in a partial-support blood pump the heart and pump both perform work, the work available to be performed by the blood pump may also be an indication of how much work the heart is performing. For example, if the pump is performing a relatively high amount of work, thereby leaving relatively little available work to be performed, the heart is likely also performing a relatively low amount of work. Conversely, if the pump is performing a relatively low amount of work, thereby leaving more available work to be performed, the heart is likely performing a relatively high amount of work.

In one embodiment, a method of estimating an amount of work available to be performed by a blood pump implanted in a patient includes calculating a first coordinate value characterizing a volume of blood impelled in the pump and a second coordinate value characterizing a differential pressure across the pump for each of a plurality of flow rate data points of a given cardiac cycle of the patient, each flow rate data point indicative of a flow rate of blood through the pump. An area enclosed by the first and second coordinate values of the plurality of flow rate data points is determined, the determined area being indicative of an amount of work available to be performed by the blood pump.

In another aspect of this embodiment, the method further include determining a starting time of the given cardiac cycle based on the determined flow rate data points crossing a running average flow rate and determining an ending time of the given cardiac cycle based on the determined flow rate data points crossing a running average flow rate, the plurality of flow rate data points of the given cardiac cycle being indicative of a flow rate of blood between the starting time and ending time.

In another aspect of this embodiment, determining the starting and ending times are further based on one of: identifying consecutive instances of the determined flow rate data points crossing the running average flow rate with a negative slope; identifying consecutive instances of the determined flow rate data points crossing the running average flow rate with a positive slope; and identifying three consecutive instances of the determined flow rate data points crossing of the running average flow rate, the first of the three consecutive instances being the starting time and the third of the three consecutive instances being the ending time.

In another aspect of this embodiment, for each of the flow rate data points of the given cardiac cycle of the patient, the calculated first coordinate value is a derivative of the flow rate data point.

In another aspect of this embodiment, for each of the flow rate data points of the given cardiac cycle of the patient, the calculated second coordinate value is a differential pressure corresponding to the flow rate data point.

In another aspect of this embodiment, the method further includes determining a rotational speed of the blood pump, wherein the second coordinate value is determined at least in part using the determined rotational speed of the blood pump.

In another aspect of this embodiment, the calculated second coordinate value is interpolated from a reference curve correlating differential pressure across the pump and flow rate through the pump for a given rotational speed of the blood pump.

In another aspect of this embodiment, the flow rate data points are determined based on a non-invasive estimation of flow rate.

In another embodiment, a method of controlling a partial-support blood pump implanted in a patient includes calculating a first coordinate value characterizing a volume of blood impelled in the pump and a second coordinate value characterizing a differential pressure across the pump for each of a plurality of flow rate data points of a given cardiac cycle of the patient, each flow rate data point indicative of a flow rate of blood through the pump. An area enclosed by the first and second coordinate values of the plurality of flow rate data points is determined, the determined area being indicative of an amount of work available to be performed by the blood pump. The determined area is compared to a predetermined value indicative of a maximum allowable amount of available work for which partial-support is maintained. A speed of operation for a motor of the blood pump is increased when the determined area is greater than the predetermined value.

In another aspect of this embodiment, the partial-support blood pump is a partial-support ventricular assist device for at least one of the left and right ventricle of the patient, and wherein the predetermined value is indicative of closure of at least one of the aortic and pulmonary valve of the patient during systole.

In yet another embodiment, a method of detecting an incipient suction condition at a blood pump implanted in an patient includes calculating a first coordinate value characterizing a volume of blood impelled in the pump and a second coordinate value characterizing a differential pressure across the pump for each of a plurality of flow rate data points of a given cardiac cycle of the patient, each flow rate data point indicative of a flow rate of blood through the pump. An area enclosed by the first and second coordinate values of the plurality of flow rate data points is determined, the determined area being indicative of an amount of work available to be performed by the blood pump. The determined area is compared to a predetermined value indicative of a maximum allowable amount of available work for which blood fills the patient's heart. When the determined area is less than the predetermined value, determining the presence of an incipient suction condition.

In another aspect of this embodiment, in response to determining the presence of an incipient suction condition, automatically decreasing a speed of operation of a motor of the blood pump.

In yet another embodiment, a method of detecting a blockage in a blood pump implanted in a patient includes at a first speed of a motor of the blood pump, calculating a first coordinate value characterizing a volume of blood impelled in the pump and a second coordinate value characterizing a differential pressure across the pump for each of a plurality of flow rate data points of a given cardiac cycle of the patient, each flow rate data point indicative of a flow rate of blood through the pump. An area enclosed by the first and second coordinate values of the plurality of flow rate data points is determined, the determined area being indicative of an amount of work available to be performed by the blood pump. The speed of the motor is increased to a second speed. At the second speed, a first coordinate value characterizing a volume of blood impelled in the pump and a second coordinate value characterizing a differential pressure across the pump for each of a plurality of flow rate data points of a given cardiac cycle of the patient is calculated, each flow rate data point indicative of a flow rate of blood through the pump. An area enclosed by the first and second coordinate values of the plurality of flow rate data points is determined, the determined area being indicative of an amount of work available to be performed by the blood pump.

In another aspect of this embodiment, the method further includes calculating a difference between the determined area at the first speed and the determined at the second speed, a smaller difference being indicative of a greater likelihood of a blockage in the blood pump.

In another aspect of this embodiment, a calculated difference of zero is indicative of a total blockage in the blood pump.

In another aspect of this embodiment, the method further includes determining whether the determined area at the first speed is at least one of greater and less than the determined area at the second speed, wherein the determined area at the first speed being less than the determined area at the second speed being indicative of a suction condition at the blood pump.

In another aspect of this embodiment, the method further includes comparing the determined area to a predetermined value indicative of a minimum allowable amount of ventricular loading, wherein the determined area being less than the predetermined value is indicative of the presence of said adverse condition.

In yet another embodiment, a method of detecting a full-support blood pump implanted in a patient transitioning to a partial-support state includes decreasing a speed of operation of the blood pump. At the decreased speed, a first coordinate value characterizing a volume of blood impelled in the pump and a second coordinate value characterizing a differential pressure across the pump for each of a plurality of flow rate data points of a given cardiac cycle of the patient is calculated, each flow rate data point indicative of a flow rate of blood through the pump. An area enclosed by the first and second coordinate values of the plurality of flow rate data points is determined, the determined area being indicative of an amount of work available to be performed by the blood pump. The determined area is compared to a predetermined value indicative of a minimum amount of available work for which the blood pump enters a partial-support state. When the calculated area is less than the predetermined value, further decreasing the speed of operation of the pump, the method is repeatedly performed until the calculated area is greater than the predetermined value.

In another aspect of this embodiment, the method further includes at a control circuit, detecting the full-support blood pump transitioning to the partial-support state. Operation of the blood pump at the partial support state for at least one cardiac cycle is maintained. After the at least one cardiac cycle, a speed of operation is increased to at least one of an original and default speed of operation.

In yet another embodiment, a control circuit for estimating an amount of work available to be performed by a blood pump implanted in a patient includes a flow rate determination circuit configured to repeatedly determine flow rate data points, each flow rate data point indicative of a flow rate of blood through the pump. A volume determination circuit configured to calculate, for each determined flow rate data point of a given cardiac cycle of the patient, a first coordinate value characterizing a volume of blood impelled by the pump is included. A pressure head determination circuit configured is included to calculate, for each determined flow rate data point of the given cardiac cycle, a second coordinate value characterizing a pressure head exerted by the pump. A pump work determination circuit configured to calculate an area enclosed by the first and second coordinate values of the flow rate data points of the given cardiac cycle is included, the calculated area is indicative of an amount of work available to be performed by the blood pump.

In another aspect of this embodiment, a flow rate average tracking circuit is configured to track a running average of the determined flow rate data points and a cardiac cycle determination circuit is configured to determine a beginning flow rate data point and an end flow rate data point of the given cardiac cycle of the patient, each of the beginning and end flow rate data points corresponding to a crossing of the determined flow rate data points over the running average.

In another aspect of this embodiment, the cardiac cycle determination circuit is configured to determine the beginning and end flow rate data points based on at least one from the group consisting of: an identification of consecutive instances of the determined flow rate data points having a negative slope and crossing the running average; an identification of consecutive instances of the determined flow rate data points having a positive slope and crossing the running average; and an identification of three consecutive instances of the determined flow rate data points crossing of the running average, wherein the first of the three consecutive instances corresponds to the beginning flow rate data point and the third of the three consecutive instances corresponds to the end flow rate data point.

In another aspect of this embodiment, for each determined flow rate data point of a given cardiac cycle of the patient, the volume determination circuit is configured to calculate the first coordinate value using a derivative of the flow rate data point.

In another aspect of this embodiment, a speed determination circuit for determining a rotational speed of the blood pump is included, wherein, for each determined flow rate data point of the given cardiac cycle, the pressure head determination circuit is configured to calculate the second coordinate value using the flow rate data point and the determined rotational speed of the blood pump.

In another aspect of this embodiment, a memory configured to store a reference file containing a correlation between flow rate and pressure head of the pump for a given operational speed is included, wherein the pressure head determination circuit is operable to determine the second coordinate value using interpolation based on the reference file.

In another aspect of this embodiment, the pump includes a housing having an axis, and a rotor disposed within the housing, the rotor being rotatable around the axis.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 2:
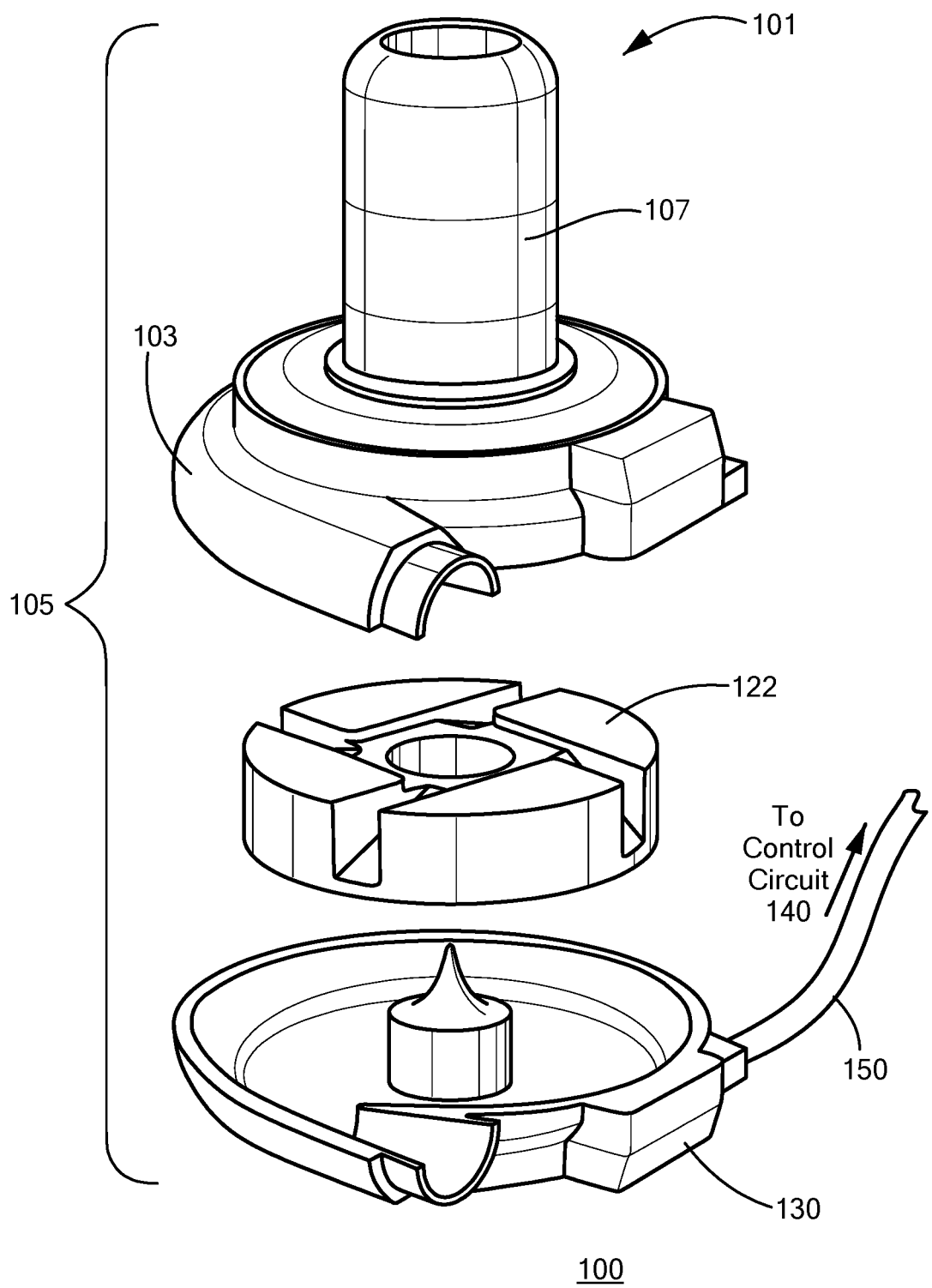
FIG. 2 is an exploded perspective view of an example blood pump system in accordance with an aspect of the disclosure.

Referring now to the drawings in which like reference designators refer to like elements, there is shown in FIG. 2 an example blood pump system 100 in accordance with one embodiment of the invention. The blood pump system 100 according to this embodiment includes a control circuit 140 (not shown) connected via a cable feed 150 to a centrifugal blood pump 101. The blood pump 101 includes a housing 105 consisting of interlocking casings to form a closed pumping chamber 103 between them. Blood is supplied to the pump 101 through an axial inlet cannula 107 adapted for apical insertion into a heart ventricle of a human or animal patient. The cannula 107 is affixed to or may be integral with the housing 105 and is in fluid flow communication with the pumping chamber 103. Blood exits the pumping chamber 103 through an outlet 113 opposite the inlet cannula 107 in a direction substantially perpendicular to the longitudinal axis of the inlet cannula 107.

Figure 1:
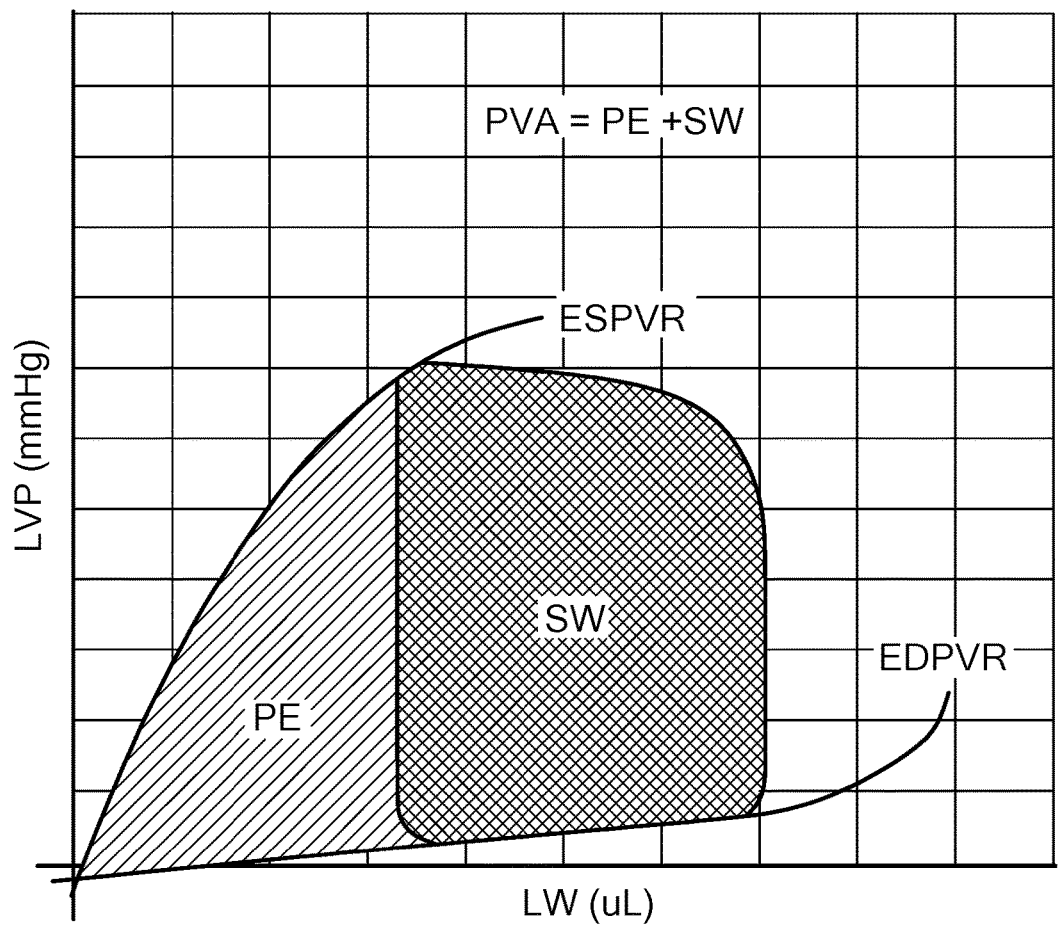
FIG. 1 is a diagram of a pressure-volume loop associated with the left ventricle of a patient.

A motor rotor or pump impeller 122 is located within the pumping chamber 103. In operation, blood entering the cannula 107 from a heart ventricle passes into the pumping chamber 103 where it is engaged by the rotating impeller 122. Blood entering the pumping chamber from the cannula 107 is redirected from axial flow exiting the cannula to a radial flow within which the impeller 122 is submerged. Although the example pump 101 of FIG. 1 is a radial flow blood pump, other types of pumps (e.g., axial flow pumps) are similarly applicable to the present disclosure.

The housing 105 of the pump may contain an electrical feed through connector 130 for a power and control cable to supply power to the electrical motor of the pump. The cable feed 150 carrying a plurality of cables is connected to the pump through the connector 130. The cables in the feed 150 may carry electrical power and control instructions to the pump 101.

Figure 3:
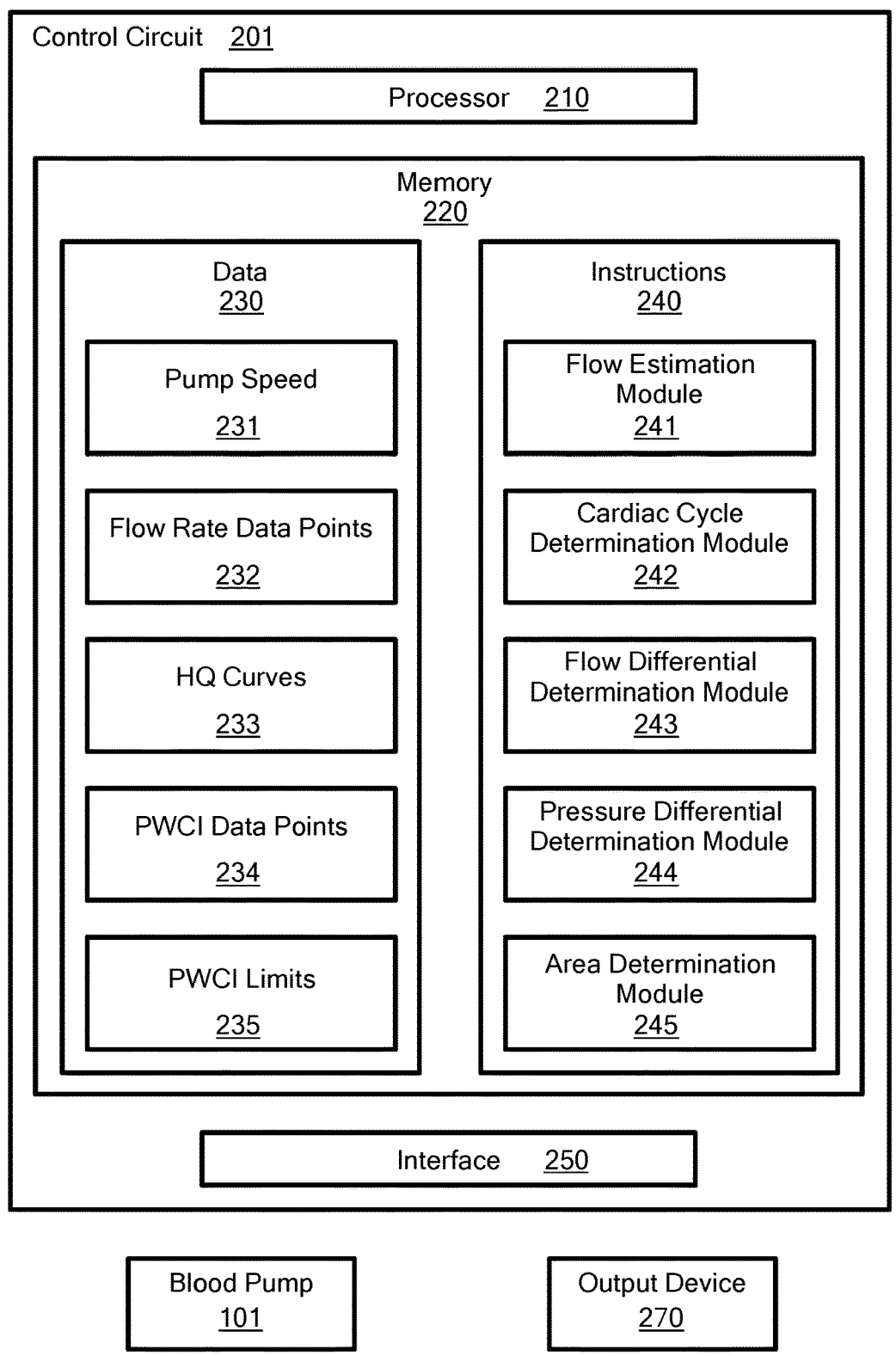
FIG. 3 is a block diagram of an example control circuit of the blood pump system of FIG. 2, in accordance with an aspect of the disclosure.

The control circuit 140 monitors and further controls operation of the pump 101. The control circuit functions may be implemented at least in part by a general-purpose processor, as shown in the example implementation of FIG. 3. As shown, an example control circuit 201 (which may be used as the control circuit 140 of FIG. 2) is implemented using a processor 210, a memory 220 and an interface 260. Memory 220 stores information accessible by processor 210, including instructions 250 that may be executed by the processor 210. The memory also includes data 230 that may be retrieved, manipulated or stored by the processor 210. The memory may be of any type capable of storing information accessible by the processor, such as a hard-drive, memory card, ROM, RAM, DVD, CD-ROM, write-capable, and read-only memories. The processor 210 may be any well-known processor, such as commercially available processors. Alternatively, the processor may be a dedicated controller such as an ASIC.

Data 230 may be retrieved, stored or modified by processor 210 in accordance with the instructions 250. The data may also be formatted in any computer-readable format such as, but not limited to, binary values, ASCII or Unicode. Moreover, the data may comprise any information sufficient to identify the relevant information, such as numbers, descriptive text, proprietary codes, pointers, references to data stored in other memories (including other network locations) or information that is used by a function to calculate the relevant data.

The control circuit 140 includes hardware and software for controlling the various aspects of the operation of the pump. The control circuit is coupled to the pump and it is operable to collect at least some of data 230 from the pump. For example, data 230 may include pump speed data 231, indicating a speed of rotation of the pump's rotor. Pump data 230 may also include flow rate data 232 indicative of a flow rate of blood being pushed through the pump (e.g., exiting the pump). As explained in greater detail in commonly owned published Patent Application Publication Nos. 2012/0245681, 2014/0100413 and 2014/0357937, as well as pending patent application Ser. No. 14/950,467, the disclosures of which are hereby incorporated herein by reference in their entirety, the flow rate data 232 may be acquired using a model for the estimation of blood flow rate. In one example, the model determines blood flow rate based in part on the acceleration of the rotor of the pump and possibly the viscosity of the patient's blood (e.g., based on hematocrit levels). Using such a model results in the estimate having a dynamic range of about 15 Hz.

In alternative embodiments, the data 230 may include further information to estimate blood flow through the pump. For example, in a centrifugal pump, the relationship between the operating current and blood flow is monotonic for the range of electrical current at which the pump may operate. Therefore, the blood flow estimate may be determined by use of a flow-to-current correlation table.

Similarly, in an axial pump, one or more flow-to-current tables may be used to estimate the blood flow rate based at least in part on a measured electrical current used to drive the pump. As explained in greater detail in commonly owned U.S. Patent Publication No. 2012/0245681, such estimates may be determined based further on the given rotor speed of the pump, a back electromotive force (BEMF) induced by the impeller on the coils of the rotor, and possibly the viscosity of the patient's blood. The estimate of blood flow may be further based at least in part on the acceleration of the rotor of the pump. Flow estimates have a dynamic range of about 15 Hz.

Additionally, different calculations and parameters may be employed to estimate a flow rate of blood. For instance, blood flow rate may be estimated algorithmically based at least in part on an operating electrical current of the pump and a predetermined hematocrit level of the blood.

In other examples, flow rate data may be collected based on other parameters indicative of flow rate. Alternatively, flow rate data may be gathered using direct measurements, such as with an ultrasonic flow meter mounted within the pump.

Data 230 may further include one or more HQ curves 233, correlating a flow rate "Q" with a differential pressure (or differential head) "H" exerted by the pump. In the case of the present disclosure, the HQ curves 233 may indicate, an expected differential pressure exerted by the pump for a given flow rate of blood exiting the pump. Because the relationship between flow rate and differential pressure varies based on pump speed, different HQ curves 233 may be stored for multiple pump speeds, preferably the speeds at which the pump operates. As explained in greater detail below, the HQ curves 233 may be used to determine a differential pressure across the pump based on measured, estimated, calculated, or otherwise determined flow rate data 233.

Figure 6:
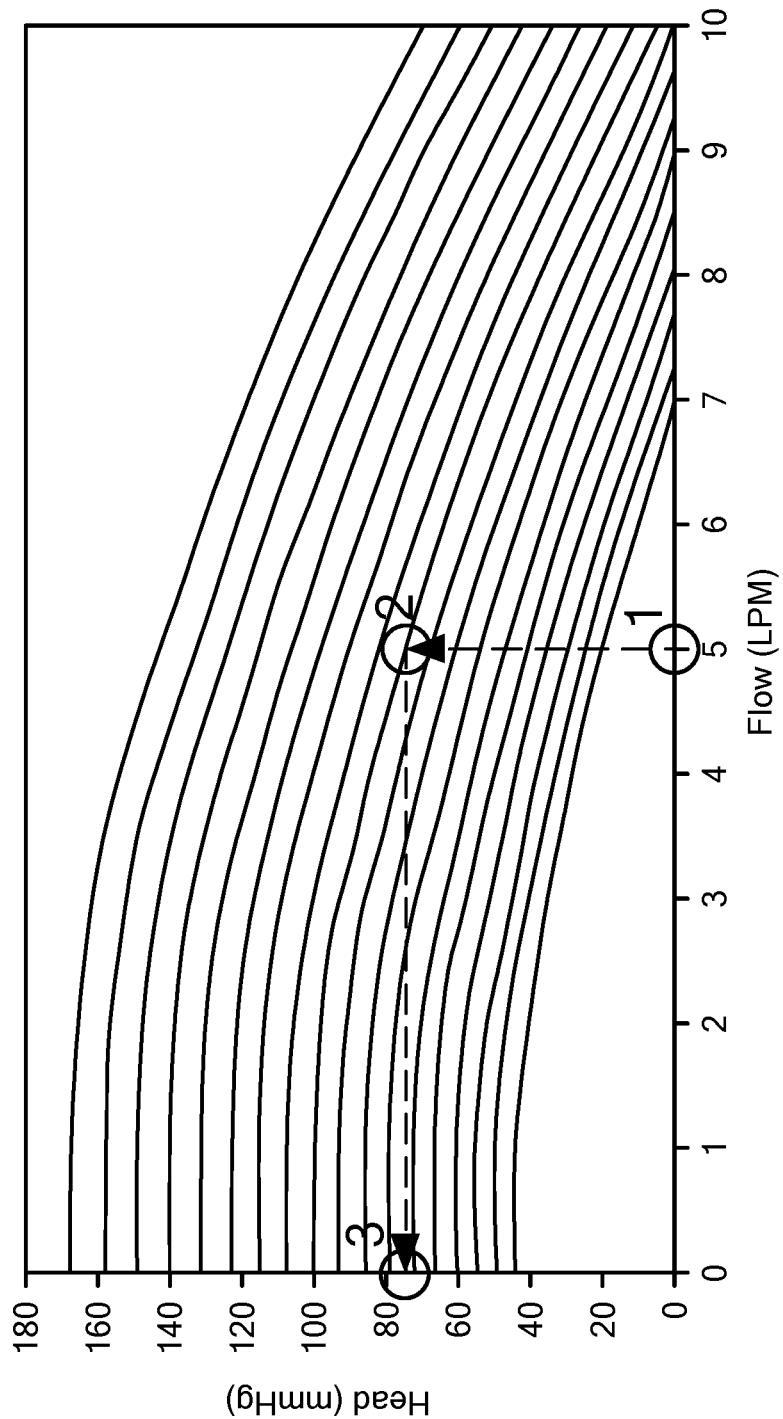
FIG. 6 is a graphical plot of differential pressure as a function of flow in accordance with an aspect of the disclosure.

FIG. 6 shows an example set of HQ curves plotting the differential pressure as a function of flow in a given pump for a plurality of operating speeds of the pump. These curves may be predetermined during development of the pump. As shown in FIG. 6, the curves may express differential pressure as a function of flow rate for a given motor speed of a given pump. Thus differential pressure across the pump may be determined based on the determined flow rate, and further based on a then-current motor speed. Generally, and regardless of motor speed, differential pressure is inversely proportionate to flow rate, such that high flow yields lower pressure head and low flow results in higher pressure head, although the inverse relationship is often non-linear. In the example of FIG. 6, a flow rate of 5 liters per minute (LPM) ("1") for a given known pump speed ("2") is shown to correspond to a pressure head of about 75 mmHg ("3") exerted by the pump.

Although the HQ curves of FIG. 6 are shown as a graphical plot, the "curves" stored in memory 220 may be stored in a different format. For instance, memory 220 may store a look-up table correlating given flow rates at a given pump speed to respective differential pressures. Then, for a given determined flow rate at a given determined pump speed, the corresponding differential pressure may be looked up in the table. Corresponding differential pressures for flow rate values not stored in the look up table may be interpolated based on the values that are stored in the table using approximations, curve fitting and/or other techniques. Alternatively, memory 220 may store an equation in which each of speed, flow rate and differential pressure are variables of the equation. Then, for given values of any two of the variables, the third variable may be calculated based on the equation.

Data 230 may yet further include pump capacity work index (PCWI) values 234. As explained in greater detail herein, the PCWI values are values characterizing an amount of work available for the pump to perform for a given one or more cardiac cycles. PCWI values 234, and particularly how they are calculated, are explained in greater detail in connection with FIGS. 4 and 5. In many cases, PCWI values may be displayed or otherwise output by an output device 270 coupled to the control circuit 201. The output may then be read by a clinician, who in turn may determine whether to adjust operation of the blood pump based on those PCWI values 234.

Optionally, if a control circuit 201 is programmed to control operation of a pump in response to calculated PCWI values 234, the data 230 may further include prestored PCWI value limits 235. These prestored, predetermined limits may be used in comparisons against the calculated PCWI values in order to draw conclusions about a given patient's health, and may be good indicators of how a patient should be treated in view of the calculated PCWI value 234 (e.g., whether it is undesirable to increase motor speed of the patient's pump). The PCWI value limits 235 may be different for different pumps and different patients, and may be preset on a patient-by-patient basis. Alternatively, the limits 235 may be set identically for all similar pumps, thereby setting standard or baseline values for guiding or otherwise controlling operation of those pumps.

The instructions 240 stored in the memory 220 may include one or more instruction sets or modules for performing certain operations in accordance with the present disclosure. One such module may be a flow estimation module 241 for performing the steps required to determine a flow rate of blood through the pump. Another such module may be a cardiac cycle determination module 242 for performing the steps required to determine a beginning point and ending point for a single cardiac cycle (or discrete number of cardiac cycles). A further such module may be a volume component determination module 243 for determining the volume component of the available pump work, and a pressure component determination module 244 for determining the pressure component of the available pump work. The instructions 240 may also include a pump work determination module 255 for calculating a PCWI value 234 based on the determined volume and pressure components of modules 243 and 244. An example PCWI value calculation is described in greater detail below.

The control circuit 201 may optionally include an interface 250 which connects the control circuit 201 to an output device 270. The interface 250 may be an analog interface (e.g., audio interface) or a digital interface, such as Bluetooth, TCP/IP, wi-fi, and others. Where the control circuit is implemented in an implantable structure adapted to be disposed within the body of the patient, the interface 250 may include known elements for communicating signals through the skin of the patient. The output device 270, may be a speaker, a light, a communications terminal (e.g., computer, cell phone), or any other type of device.

Although FIG. 2 functionally illustrates the processor and memory as being within the same block, it will be understood that the processor and memory may actually comprise multiple processors and memories that may or may not be stored within the same physical housing. The memory may include one or more media on which information can be stored. Preferably, the medium holding the instructions retains the instructions in non-transitory form. Some or all of the instructions and data may be stored in a location physically remote from, yet still accessible by, the processor. Similarly, the processor may actually comprise a collection of processors which may or may not operate in parallel.

Figure 4:
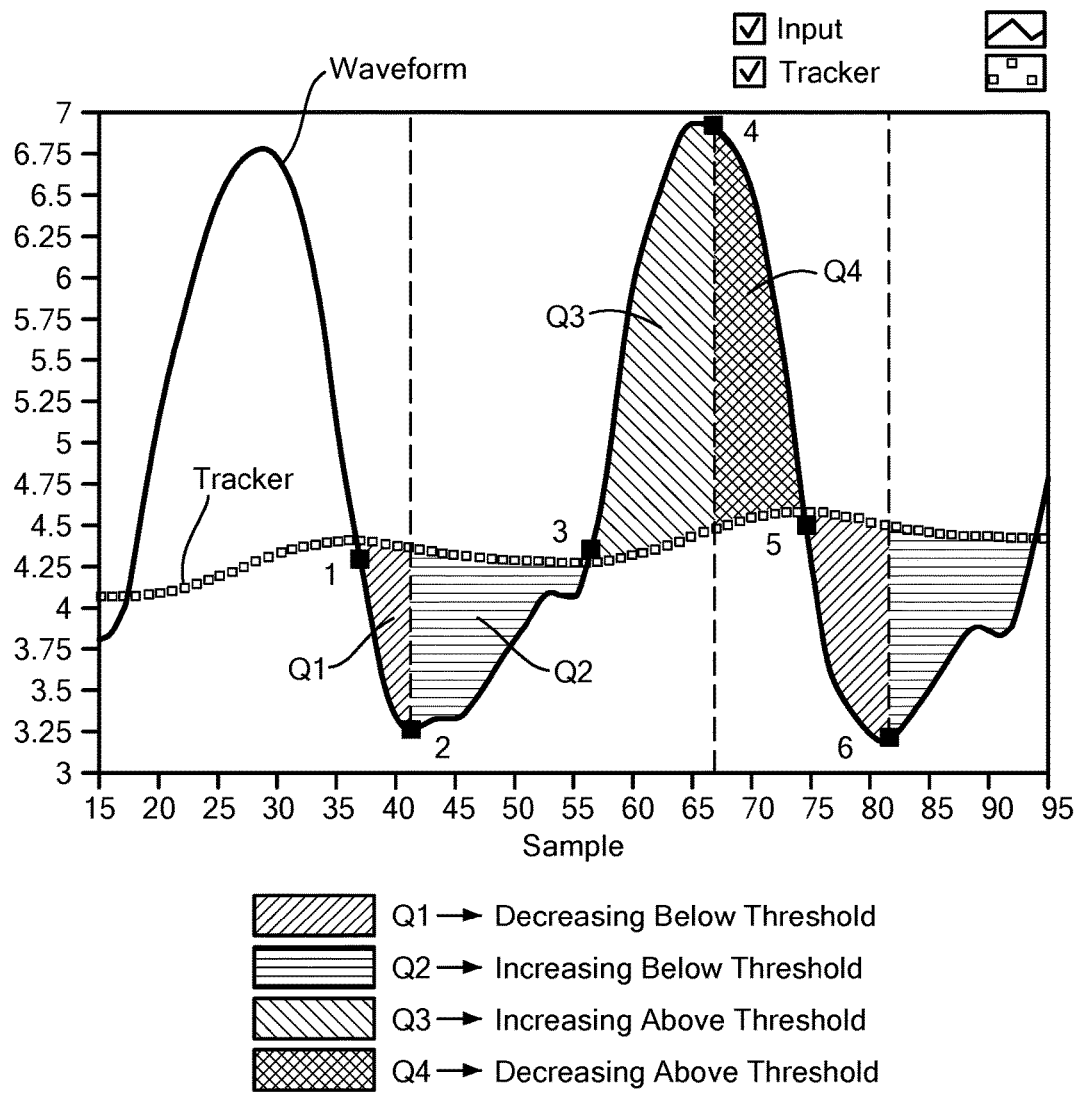
FIG. 4 is a graphical plot of flow rate of blood through a blood pump over time, in accordance with an aspect of the disclosure.
Figure 5:
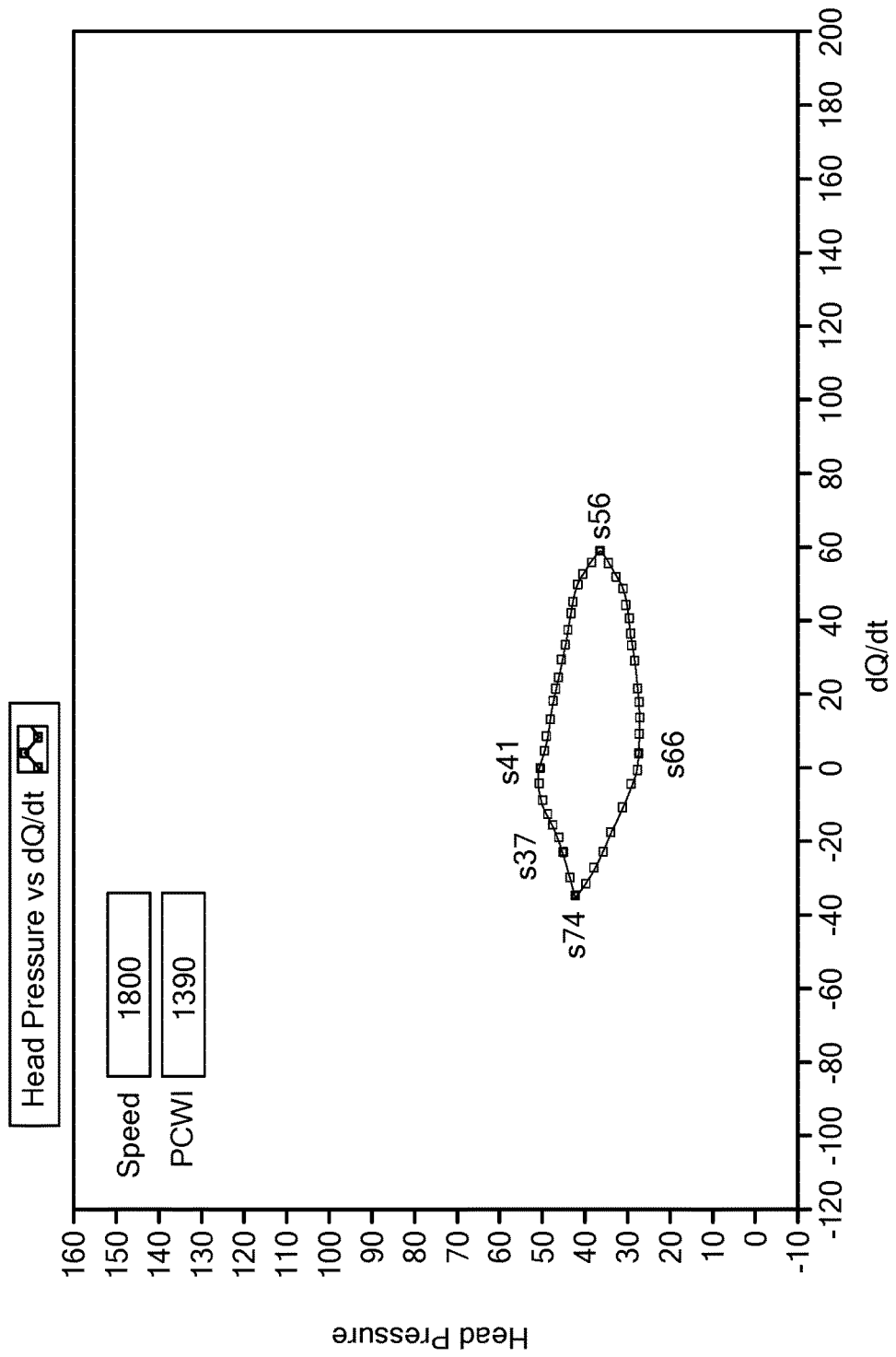
FIG. 5 is a graphical plot of a measure of volume and a measure of pressure of a blood pump in accordance with an aspect of the disclosure.

An example operation of the control circuit 201 is illustrated by way of the graphical representations of FIGS. 4 and 5. FIG. 4 is a graphical plot of an instantaneous flow rate of blood through a blood pump over time. Shown in FIG. 4 are about 95 flow rate data points which form a quasi-sinusoidal wave ("Waveform"). Each flow rate data point represents a then-instant flow rate of blood exiting a blood pump. In this example, the blood pump is operating in parallel with the patient's heart. The flow rate through the pump increases during systole, because the inlet of the pump is exposed to the pressure exerted by the heart as it contracts. Conversely, the flow rate decreases during diastole. Thus, flow rate varies over the course of a cardiac cycle, such that a full period of the sinusoid corresponds to a single cardiac cycle.

Also shown in FIG. 4 are a corresponding number of average flow rate data points that form another quasi-sinusoidal wave ("Tracker"). In the example of FIG. 4, the average flow rate data points are based on a running average, which averages a predetermined number of previously determined flow rate data points, or the flow rate data points previously collected over a predetermined window of time. As shown in FIG. 4, the running flow rate average also varies over time, although not by as much as the then-instant flow rate data.

As shown in FIG. 4, a single cardiac cycle may begin at point "1" (corresponding to data point s37), in which flow rate is decreasing, and has just dropped below the average flow rate. This indicates the end of systole for a previous cardiac cycle and beginning of diastole for the next cardiac cycle. Point "2" (corresponding to data point s41) indicates a time at which flow rate begins to increase, but is still less than the average flow rate. At point "3" (corresponding to data point s56), flow rate continues to increase and has just increased above the average flow rate, indicating the end of diastole and beginning of systole of the current cardiac cycle. At point "4" (corresponding to data point s66), flow rate begins to decrease, but remains greater than average flow rate. Lastly, at point "5" (corresponding to data point s74) flow rate continues to decrease and drops below the tracked average flow rate, indicating the end of systole for the current cardiac cycle and beginning of diastole for the next cardiac cycle. In this manner, points "1" and "5" may be considered to mark the beginning and end of a single cardiac cycle. In other examples, a cardiac cycle may be considered to "begin" and "end" at a different phase of the cycle (e.g., end of diastole, peak flow, minimum flow, etc.), so long as the beginning and ending mark similar phases of a complete cycle. Points "2" through "4" may further be used to keep track of progression of the cycle, so that it is clear that a full cycle has been completed.

FIG. 5 is a graphical plot of an example PCWI curve based on the waveform of FIG. 4. Each of the data points shown in FIG. 5 corresponds to a data point (s37 through s74) of the waveform of FIG. 4. Each data point is shown in FIG. 4 as being plotted along each of a horizontal axis (volume component) and a vertical axis (pressure component), much the same way a pressure-volume loop is conventionally drawn. In the example of FIG. 4, the volume component is a second derivative of the volume of blood exiting by the pump, i.e., the first derivative of the flow rate through the pump over time. Stated another way, the volume component dQ/dt is the slope of the waveform of FIG. 4 at the time of the given data point. Also, in the example of FIG. 4, the pressure component is a differential pressure across the blood pump (or pressure head exerted by the pump) at the time of the given data point. As explained above and shown in FIG. 6, differential pressure and/or pressure head may be expressed as a function of flow rate for a given motor speed of a given pump.

As an example, FIG. 4 shows that each of data points s37 and s74 has a decreasing slope and an average flow rate, corresponding to a negative derivative of flow rate and midrange differential pressure. Similarly, data point s41 corresponds to a maximum flow, at which the slope of the flow waveform is about 0, and differential pressure is at a minimum. Data point s56 has an increasing slope and an average flow rate, corresponding to a positive derivative of flow rate and midrange differential pressure. And data point s66 corresponds to a minimum flow, at which the slope of the flow waveform is about 0, and differential pressure is at a maximum.

Plotting each flow rate data point on the volume-pressure axes of FIG. 5 effectively converts the flow rate data points into PCWI data points, also referred to herein as PCWI coordinates. The PCWI data points may be considered to enclose an area of the pressure component/volume component coordinate space of FIG. 5. This is illustrated in FIG. 5 by connecting PCWI data points in the time-based order of their corresponding flow rate data points to form a curve. Under normal operation of the pump, the curve may be expected to look something like the curve in FIG. 5, with cyclically increasing and decreasing flow rate derivative, and a cyclically increasing and decreasing differential pressure out of phase with the changes in flow derivative by about 90 degrees (thereby forming an enclosed area). The area of the enclosed space may be determined by any conventional means for estimating, calculating or otherwise determining the area of a polygon.

The example systems (control circuits and/or processors) described above may be operable to determine PCWI values, as demonstrated above, using the operations of the example methods described herein. It should be understood that the following operations do not have to be performed in the precise order described below. Rather, various operations can be handled in a different order or simultaneously. It should also be understood that these operations do not have to be performed all at once. For instance, some operations may be performed separately from other operations. Moreover, operations may be added or omitted.

Figure 7:
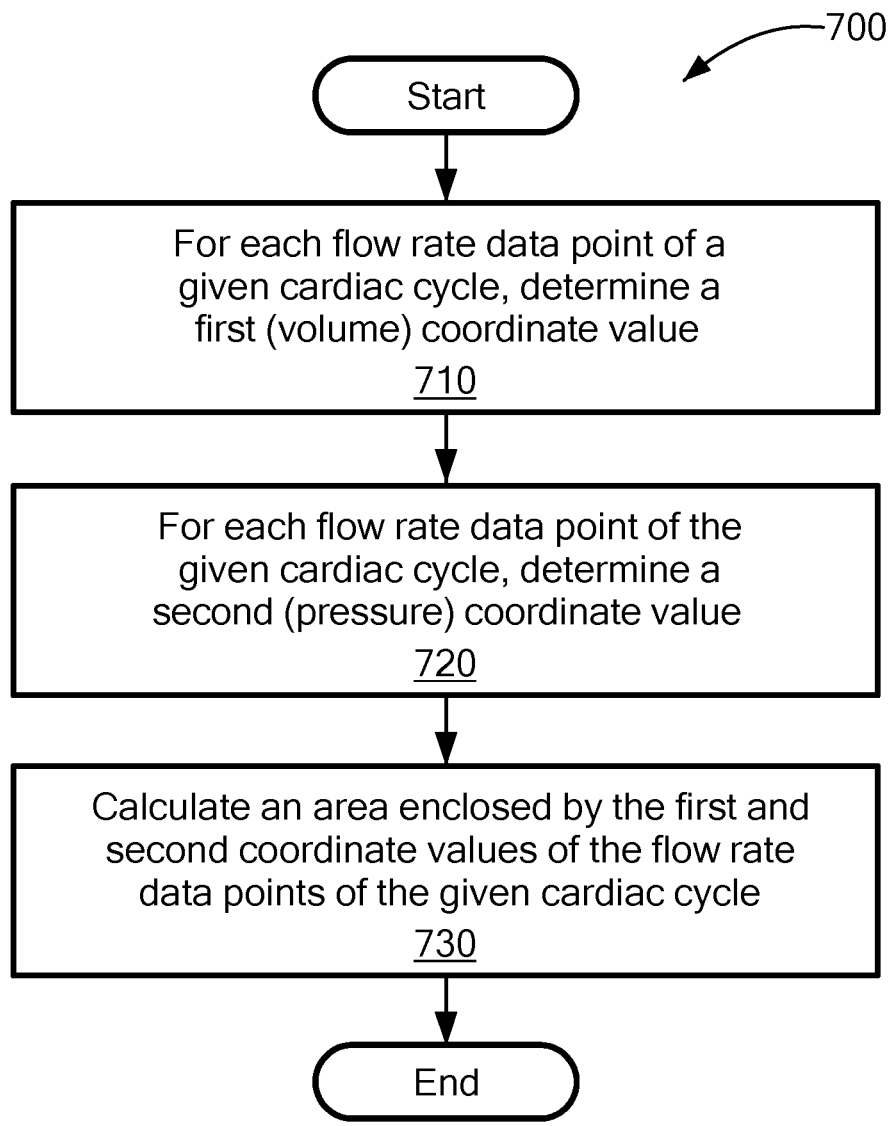
FIG. 7 is a flow diagram of an example method for determining a pump capacity work index in accordance with an aspect of the disclosure.

FIG. 7 is a flow diagram of a routine 700 for determining a PCWI value. Routine 700 begins at 710 with, for each of the flow rate data points of a given cardiac cycle, determination of a first coordinate value. The first coordinate value may be a characterization of a volume of blood impelled by the blood pump, such as a derivative of a flow rate of blood through the pump (dQ/dt). At 720, for each of the flow rate data points of the given cardiac cycle, a second coordinate value is also determined. The second coordinate value may be a characterization of pressure exerted by the pump, such as a differential pressure across the pump. The first and second coordinate values may effectively map the flow rate data point to a pressure-volume coordinate plane of the blood pump. Thus, repeating the coordinate transfer of 710 and 720 for each flow rate data point of the given cardiac cycle yields a loop or enclosed space that effectively represents a pressure-volume loop of the blood pump. At 730, an area of the enclosed space is calculated. The calculated area is the PCWI value.

Figure 8:
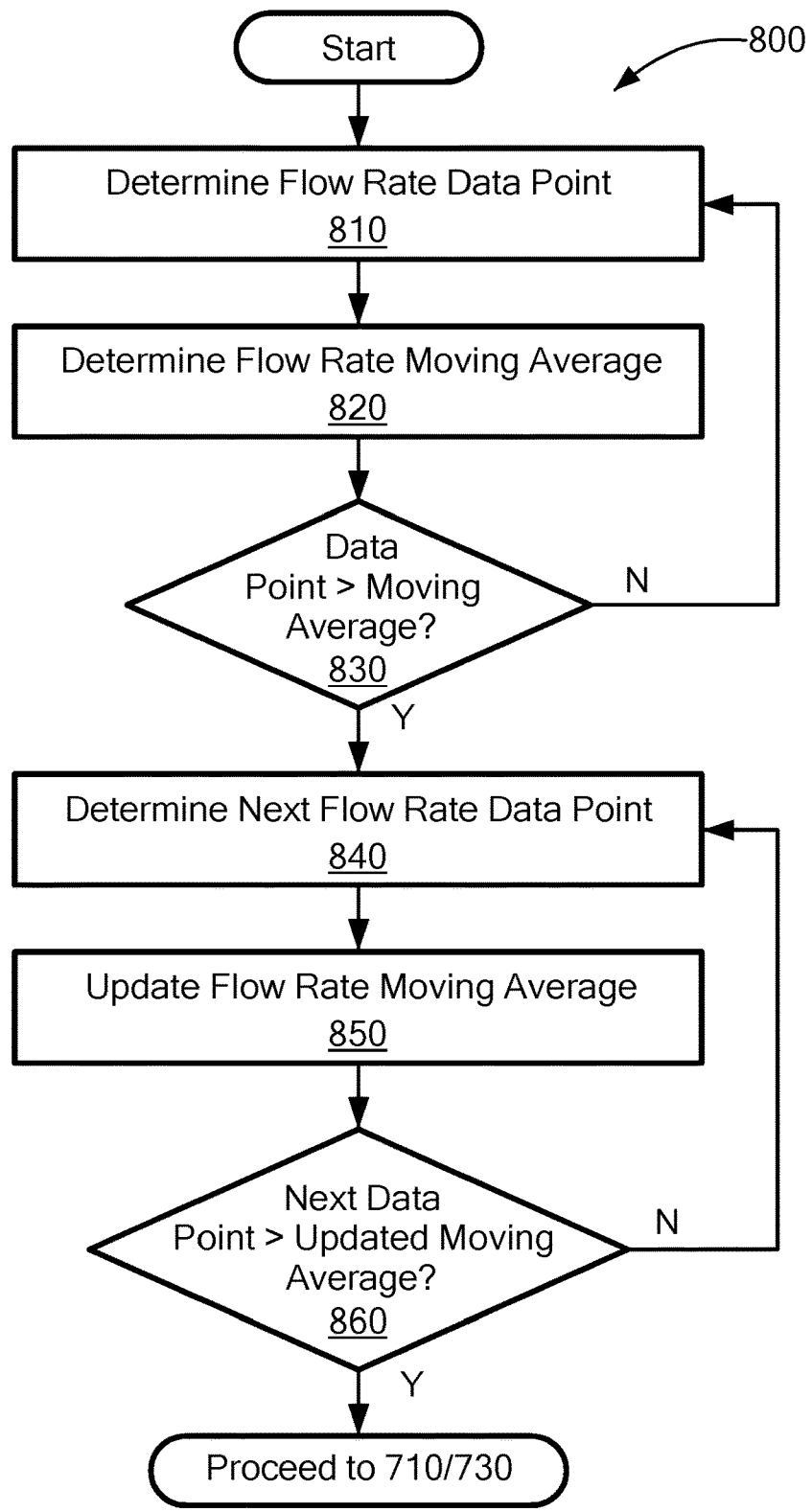
FIG. 8 is a flow diagram of an example method for identifying a single cardiac cycle based on flow rate data, in accordance with an aspect of the disclosure.

The routine 700 of FIG. 7 may further involve determining a starting and ending point of the given cardiac cycle, such that the operations of FIG. 7 may begin with the starting point of the given cardiac cycle and end with the ending point thereof. FIG. 8 is a flow diagram of an example routine 800 for determining a starting point and/or ending point of a cardiac cycle. At 810, a first flow rate data point is determined. At 820, a flow rate moving average is updated based on the first flow rate data point. At 830, the flow rate data point is compared to the moving average to determine which is greater. If the moving average is greater, operations revert to 810 with determination of another flow rate data point until a flow rate data point is found to be greater than the moving average. If the flow rate data point is found to be greater than the moving average, then at 940, a next flow rate data point is determined, and at 850 the moving average is updated based on said next flow rate data point. At 860, said next flow rate data point is compared to the updated moving average to determine which is less. If the moving average is less than the flow rate data point, operations revert to 840 with determination of another flow rate data point until a flow rate data point is found to be less than the moving average. If the flow rate data point is found to be less than the moving average, indicating that consecutive flow rate data points have crossed the moving average with a negative slope, then the beginning or ending time of the cardiac cycle has been identified, and thus corresponds to the first flow rate data point that is found to be less than the moving average. Operations may then resume with either 710 (for a starting time) or 730 (for an ending time) of FIG. 7.

The example routine 800 of FIG. 8 particularly demonstrates identifying starting and ending times for a cardiac cycle beginning and ending with a transition from systole to diastole. However, similar methods may be employed to identify starting and ending times for other cardiac cycles. For instance, a cardiac cycle beginning and ending with transition from diastole to systole may be identified by looking for a transition from below the moving average to above the moving average (stated another way, consecutive flow rate data points with a positive slope crossing over the moving average). For further instance, a cardiac cycle beginning and ending with peak or maximum flow may first look for increases in flow rate followed by a decrease in flow rate. Similarly, a cardiac cycle beginning and ending with minimum flow may first look for decreases in flow rate followed by an increase in flow rate.

First and second coordinates may be calculated and plotted for each of the flow rate data points associated with the starting and ending times collected for the flow rate data point corresponding to the ending time. In such a case, the ending time flow rate data point may be approximately equal to the starting time flow rate data point, such that that the PCWI loop is closed by connecting each of the PCWI coordinate points to one another. Alternatively, if the beginning and ending flow rate data points are not approximately equal, and the PCWI loop is still not fully closed, the loop may be closed based on an approximation. As a further alternative, first and second coordinates may be calculated and plotted for the flow rate data points from the starting time to one data point preceding the ending time, such that the PCWI coordinate points corresponding to those flow rate data points are connected in a loop. Or first and second coordinates may be calculated and plotted for the flow rate data points from one data point after the starting time to the ending time, such that the PCWI coordinate points corresponding to those flow rate data points are connected in a loop.

In some cases, a beginning and ending of a cardiac cycle may be detected without considering slope of the flow rate data points. For instance, a first instance of consecutive flow rate data points crossing over the moving average may be identified. In such a case, a second instance of crossover may indicate a midpoint of the cardiac cycle, and a third instance of crossover may indicate completion of the cardiac cycle. Alternatively, as described in connection with FIG. 4, the cardiac cycle may be identified by looking for each of (i) a decrease between consecutive flow rate data points occurring below the moving average, (ii) an increase below the moving average, (iii) an increase above the moving average, (iv) a decrease above the moving average, and finally (v) another decrease below the moving average to complete the cardiac cycle.

As a further alternative, the beginning and end of the cardiac cycle may be determined based on data other than flow rate data. For instance, EKG data may be used to identify a cardiac cycle, and the beginning and end of the cardiac cycle may be defined as any points of consecutive cardiac cycles having the same phase within the cycle.

Also, the example of FIG. 8 (as well as in FIG. 4) shows the moving average being updated as frequently as flow rate data points are collected. However, in other examples, the moving average may be updated with less frequency (e.g., every other flow rate data point, every third flow rate data point, every fifth flow rate data point, etc.) or could be updated based on a clock instead of the number of flow rate data points collected (e.g., every tenth of a second, every quarter second, etc.).

The example PCWI values described above are particularly beneficial because they are based entirely on measurements and determinations that can be conducted non-invasively, using instrumentation incorporated into the implanted blood pump and algorithms and data programmed and stored in electronics coupled to and in communication with the blood pump.

FIGS. 9-14A and 9-14B demonstrate the effectiveness of the above example PCWI examples, as shown in comparison with invasive measurements. FIG. 9A shows a pressure-volume loop (bold line) superimposed over a PCWI curve (thin line) for a blood pump operating at a speed of 2,000 RPM. The pressure-volume loop may be derived using catheter-based invasive measurements, whereas the PCWI curve may be derived exclusively from non-invasive measurements. As shown in FIG. 9A, the pressure-volume loop encloses a relatively large area, indicating that the heart is performing a commensurate amount of work. At the same time, the PCWI curve has a relatively large area of about 1510 (for units of $mmHg*mL/sec^2$), indicating that there is more work available for the pump to perform.

Figure 9A:
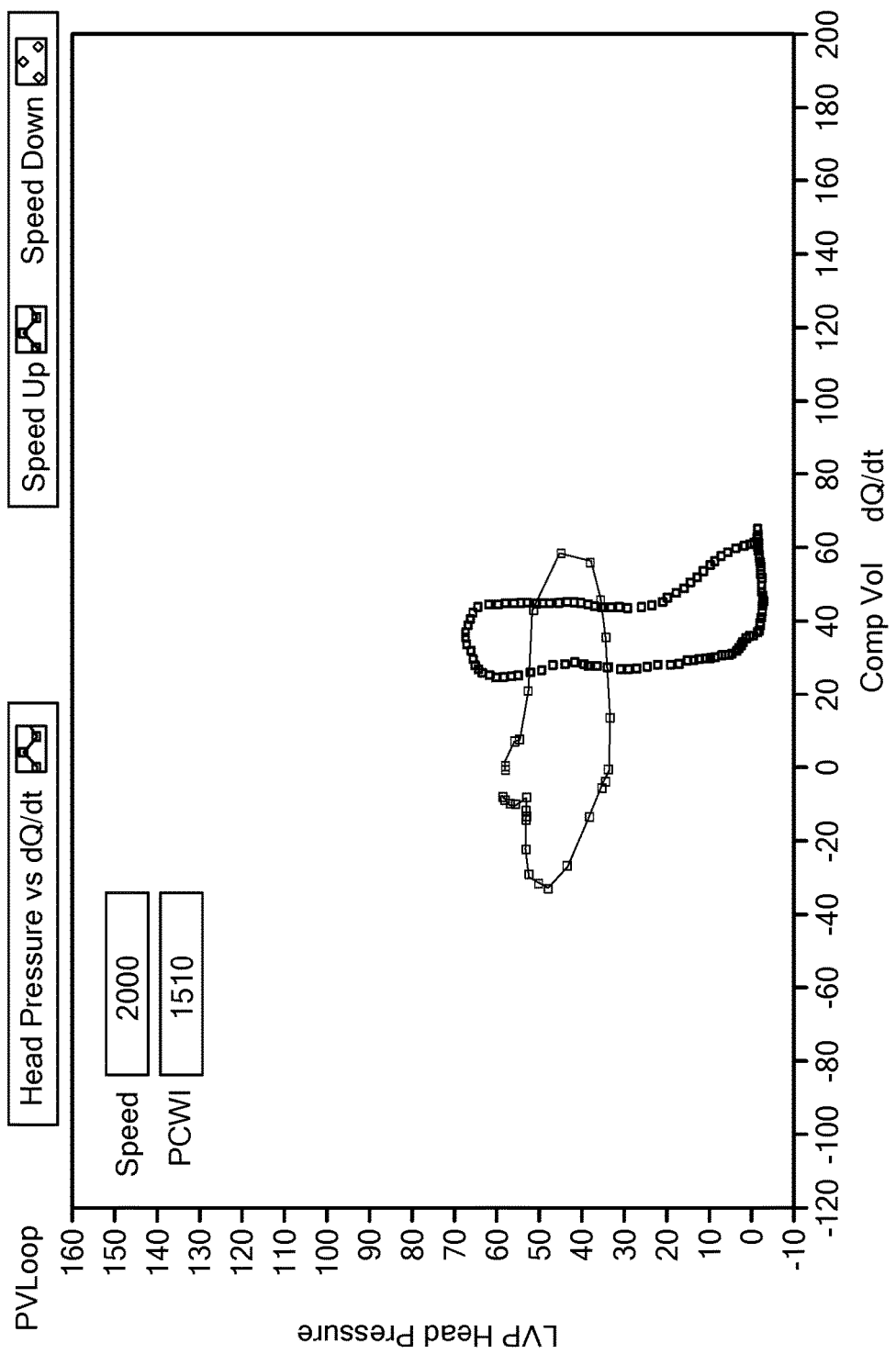
FIG. 9A, is a graphical plot of a measure of volume and a measure of pressure of a blood pump operating at a speed of 2,000 RPM.
Figure 9B:
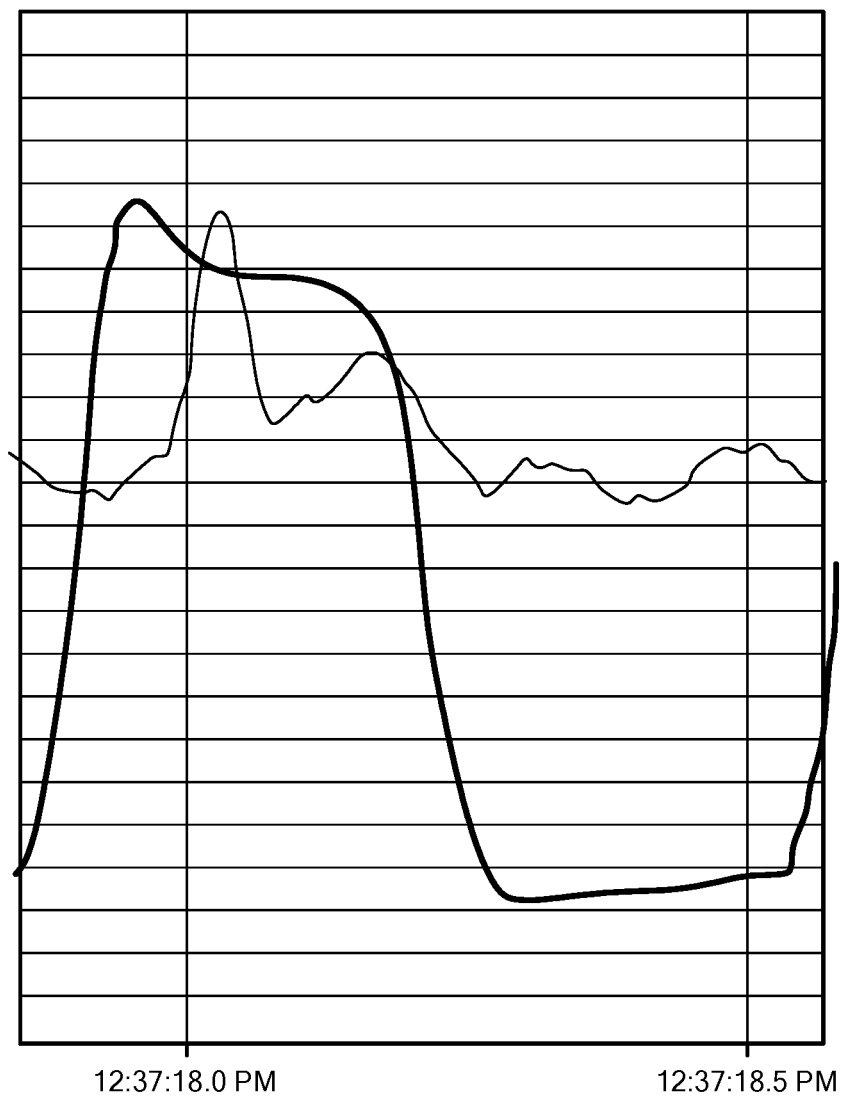
FIG. 9B is a graphical plot of left ventricular and aortic pressure of a patient using a blood pump operating at a speed of 2,000 RPM.

FIG. 9B shows invasive hemodynamic measurements of LVP (black line) and AOP (grey line) for a patient using the blood pump of FIG. 9A. As shown in FIG. 9B, under an operating speed of 2,000 RPM, the LVP and AOP measurements cross over one another, indicating that the aortic valve is open during systole.

Figure 10A:
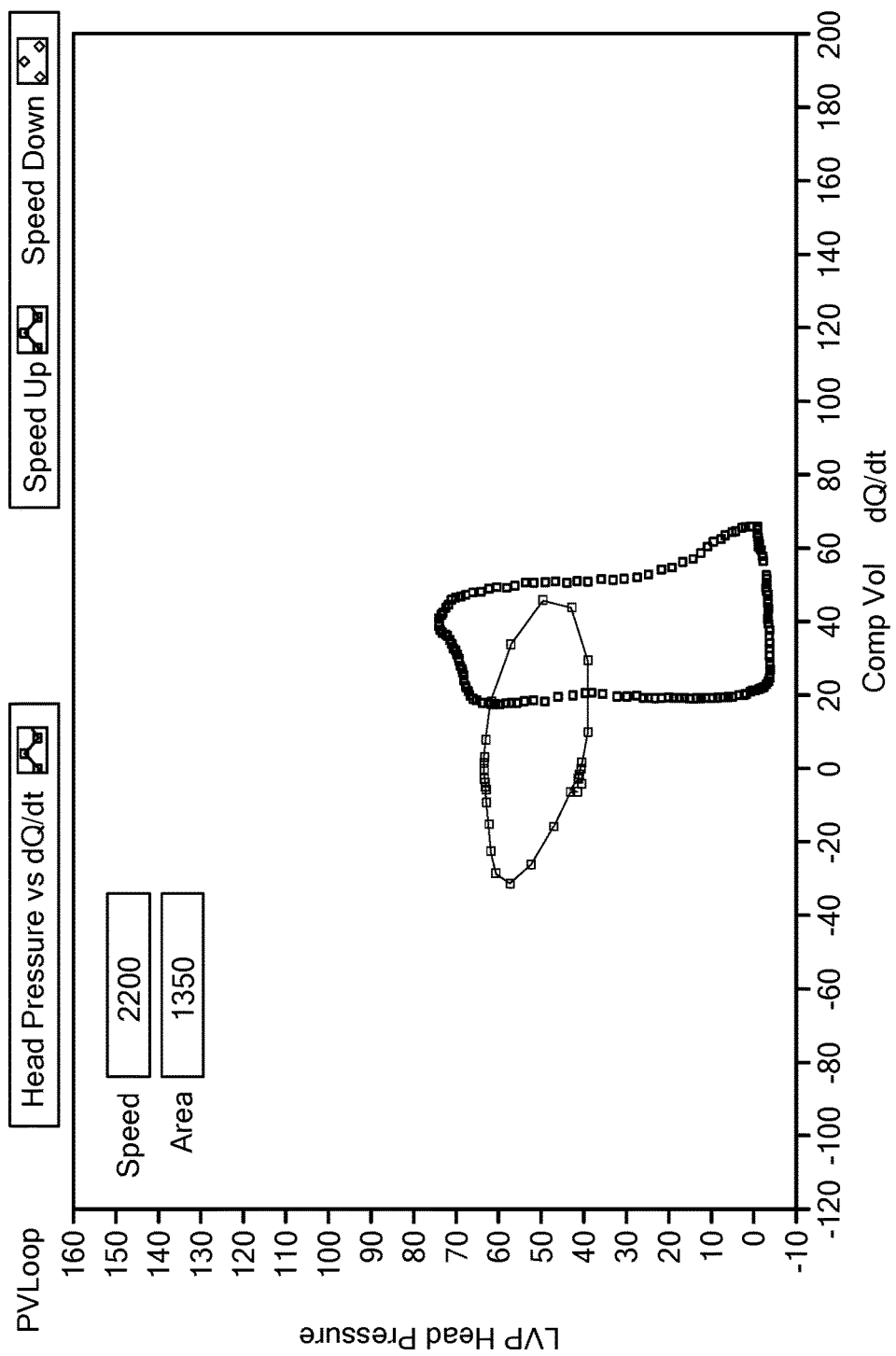
FIG. 10A, is a graphical plot of a measure of volume and a measure of pressure of a blood pump operating at a speed of 2,200 RPM.

FIG. 10A shows another pressure-volume loop (bold line) superimposed over a PCWI curve (thin line), now for the same blood pump operating at a speed of 2,200 RPM. As shown in FIG. 10A, the pump has been sped up and is performing more work, leaving less work for the heart to perform. At the same time, the PCWI curve also has a slightly smaller area, now of about 1350, indicating that the pump has taken on some of the previously available work, and now there is less available work.

Figure 10B:
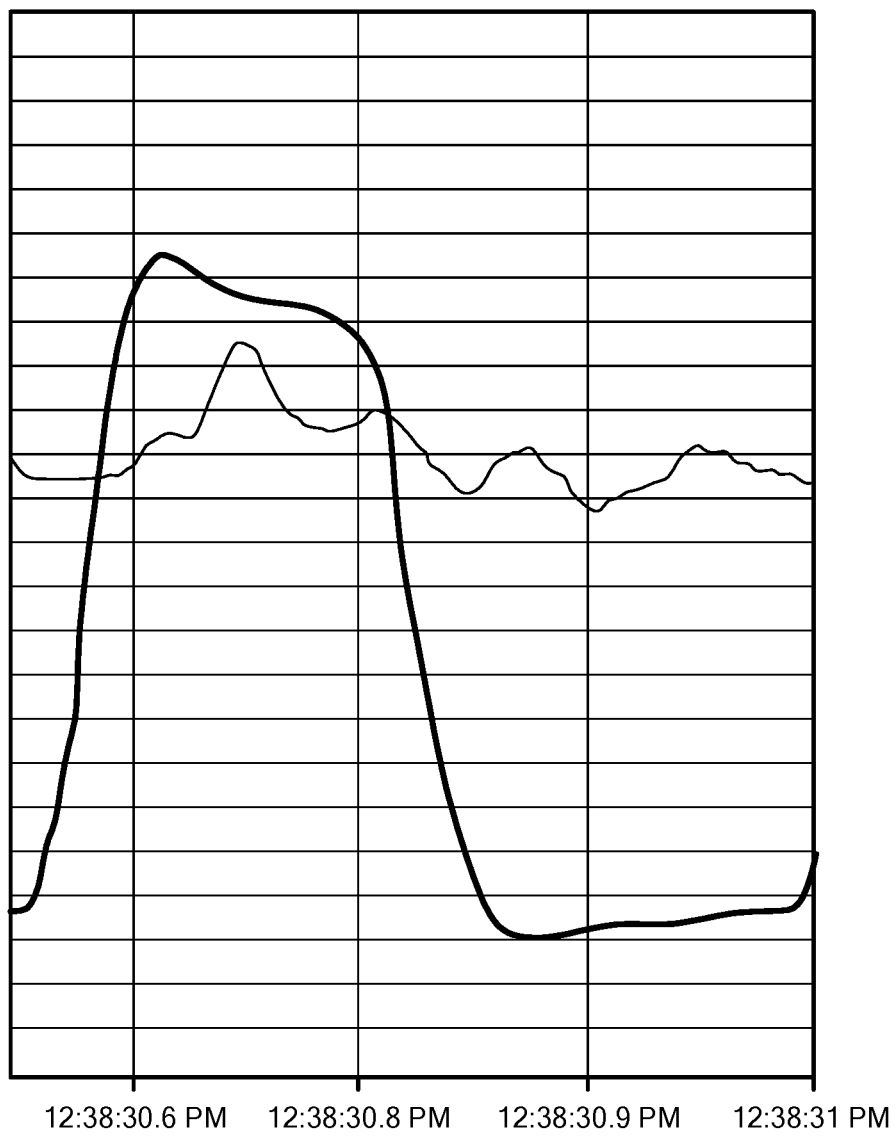
FIG. 10B is a graphical plot of left ventricular and aortic pressure of a patient using a blood pump operating at a speed of 2,200 RPM.

FIG. 10B shows invasive hemodynamic measurements of LVP (black line) and AOP (grey line) for a patient using the blood pump of FIG. 10A. As shown in FIG. 10B, under an operating speed of 2,200 RPM, the LVP and AOP measurements still cross over one another, indicating that the aortic valve is open during systole.

Figure 11A:
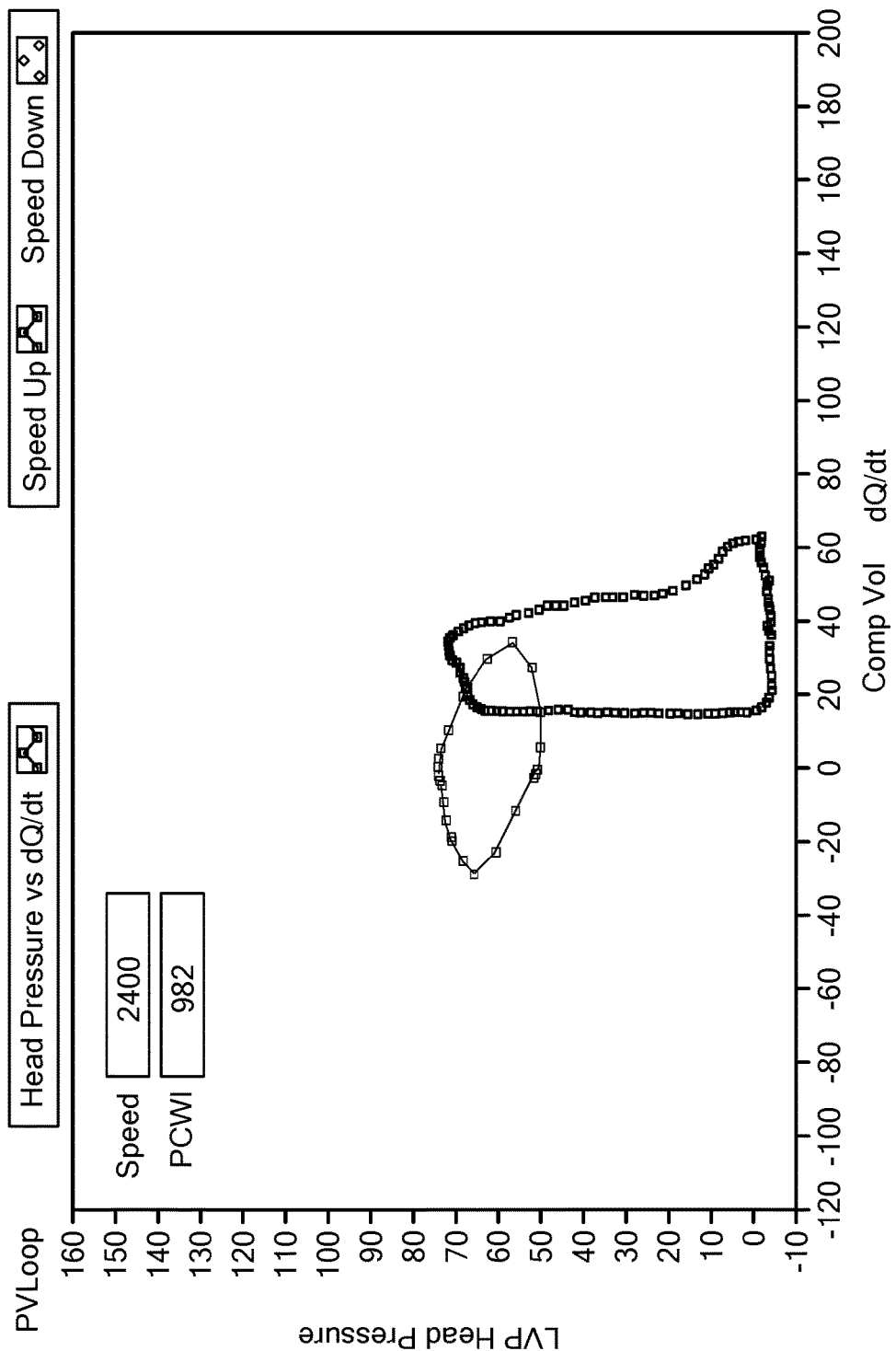
FIG. 11A, is a graphical plot of a measure of volume and a measure of pressure of a blood pump operating at a speed of 2,400 RPM.

FIG. 11A shows yet another pressure-volume loop (bold line) superimposed over a PCWI curve (thin line), now for the same blood pump operating at a speed of 2,400 RPM. As shown in FIG. 11A, the pressure-volume loop encloses an even smaller area than the pressure-volume loop of FIG. 10A, since the pump has been further sped up and is performing even more work, leaving even less work for the heart to perform. Likewise, the PCWI curve encloses an even smaller area, now about 982, indicating that the pump has again taken on some of the previously available work, leaving even less potential work.

Figure 11B:
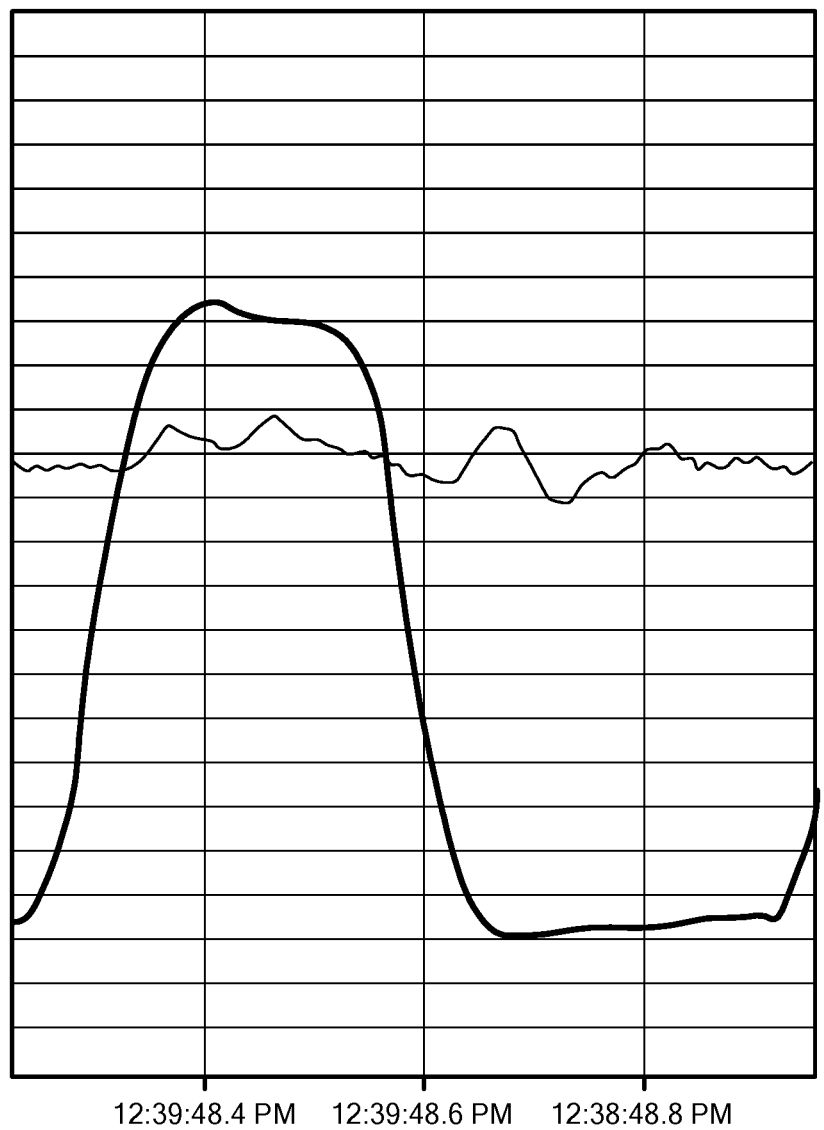
FIG. 11B is a graphical plot of left ventricular and aortic pressure of a patient using a blood pump operating at a speed of 2,400 RPM.

FIG. 11B shows that, under an operating speed of 2,400 RPM, the LVP and AOP measurements still cross over one another, meaning that the aortic valve is still open during systole.

Figure 12A:
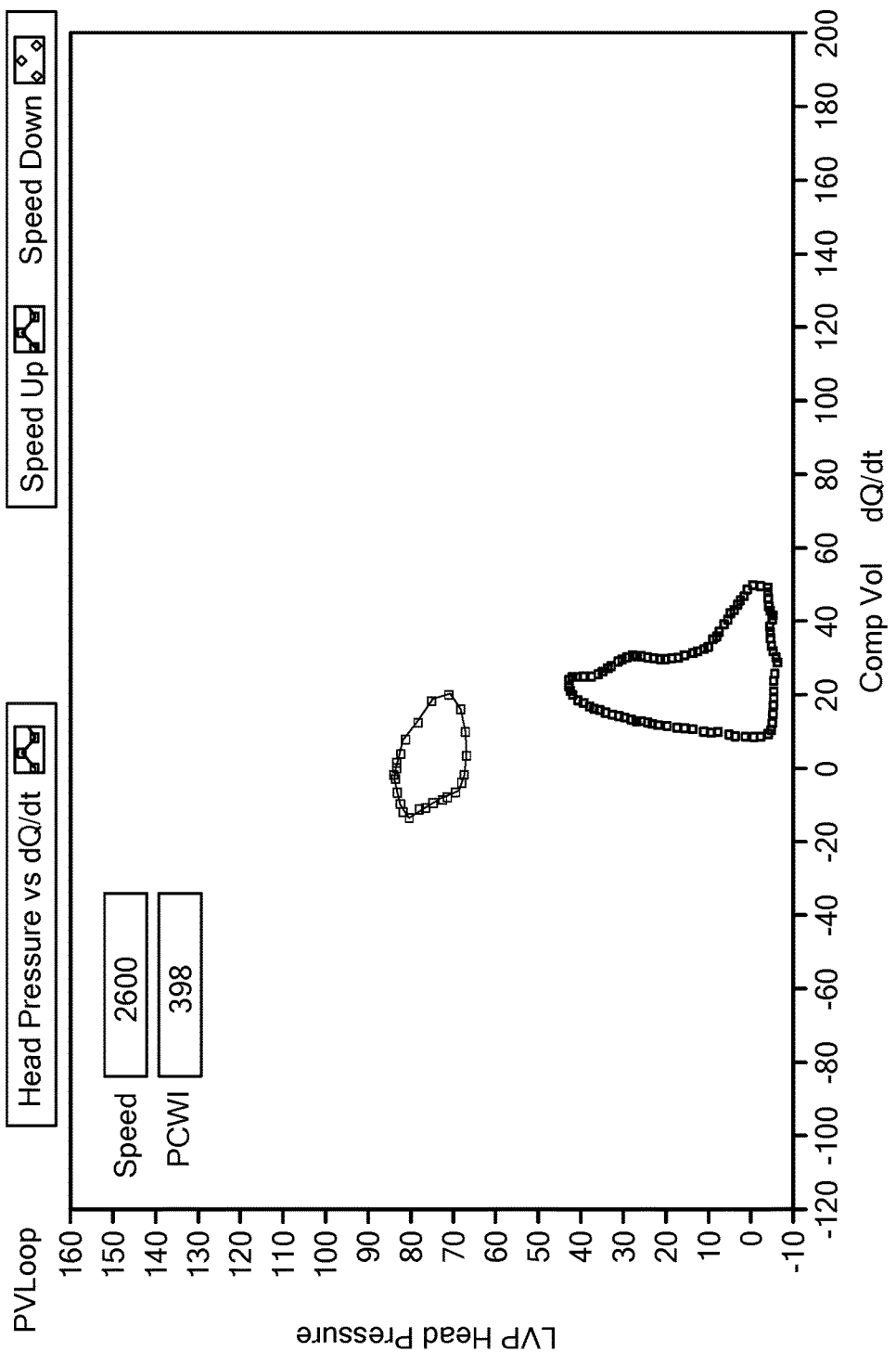
FIG. 12A, is a graphical plot of a measure of volume and a measure of pressure of a blood pump operating at a speed of 2,600 RPM.
Figure 12B:
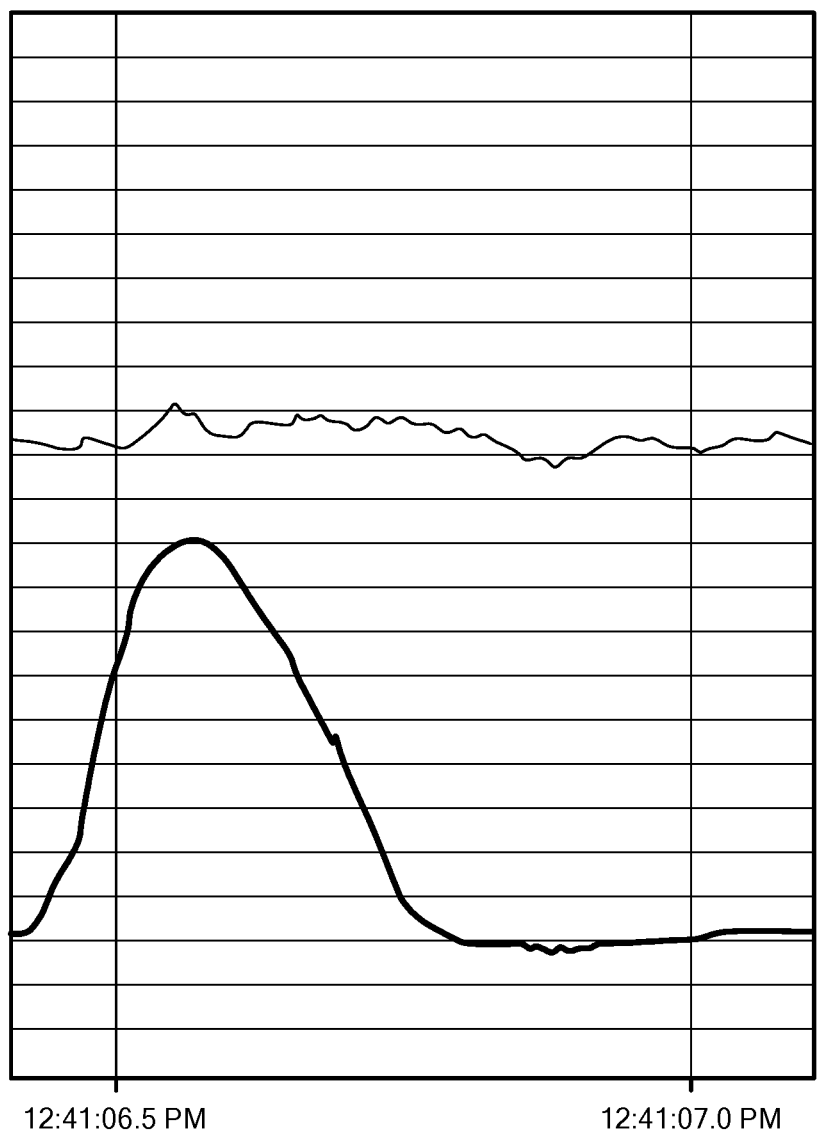
FIG. 12B is a graphical plot of left ventricular and aortic pressure of a patient using a blood pump operating at a speed of 2,600 RPM.

In FIG. 12A, the operating speed of the blood pump has been increased to 2,600 RPM, causing the pressure-volume loop to further shrink, and in turn causing the PCWI curve, to further shrink to an area of about 398. Notably, in FIG. 12B, LVP and AOP no longer cross over one another, indicating that that 2,600 RPM, the blood pump has taken on so much work that there is not enough work left at the heart for the heart to force open the aortic valve and eject blood from the left ventricle during systole.

Figure 13A:
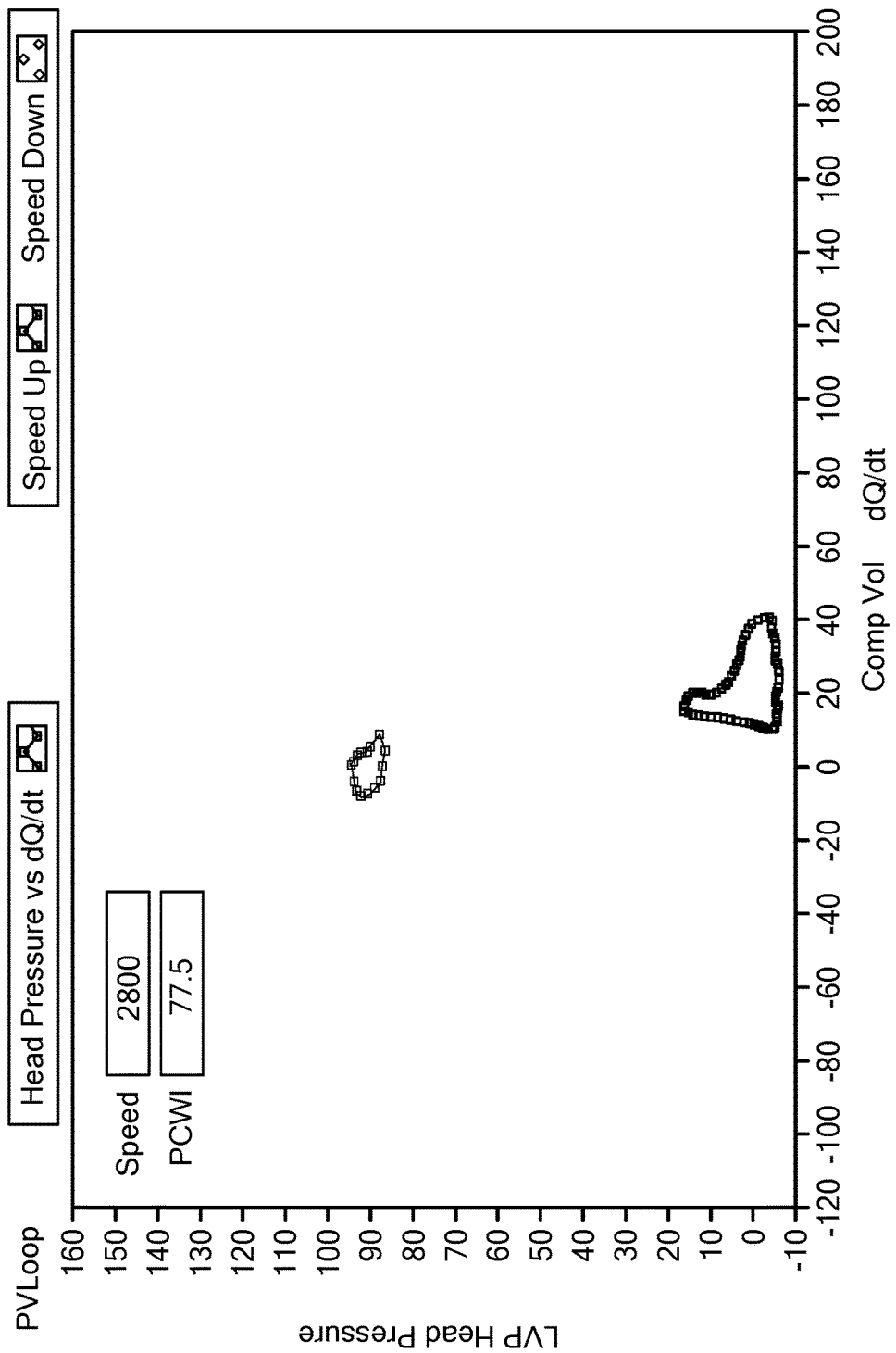
FIG. 13A, is a graphical plot of a measure of volume and a measure of pressure of a blood pump operating at a speed of 2,800 RPM.
Figure 13B:
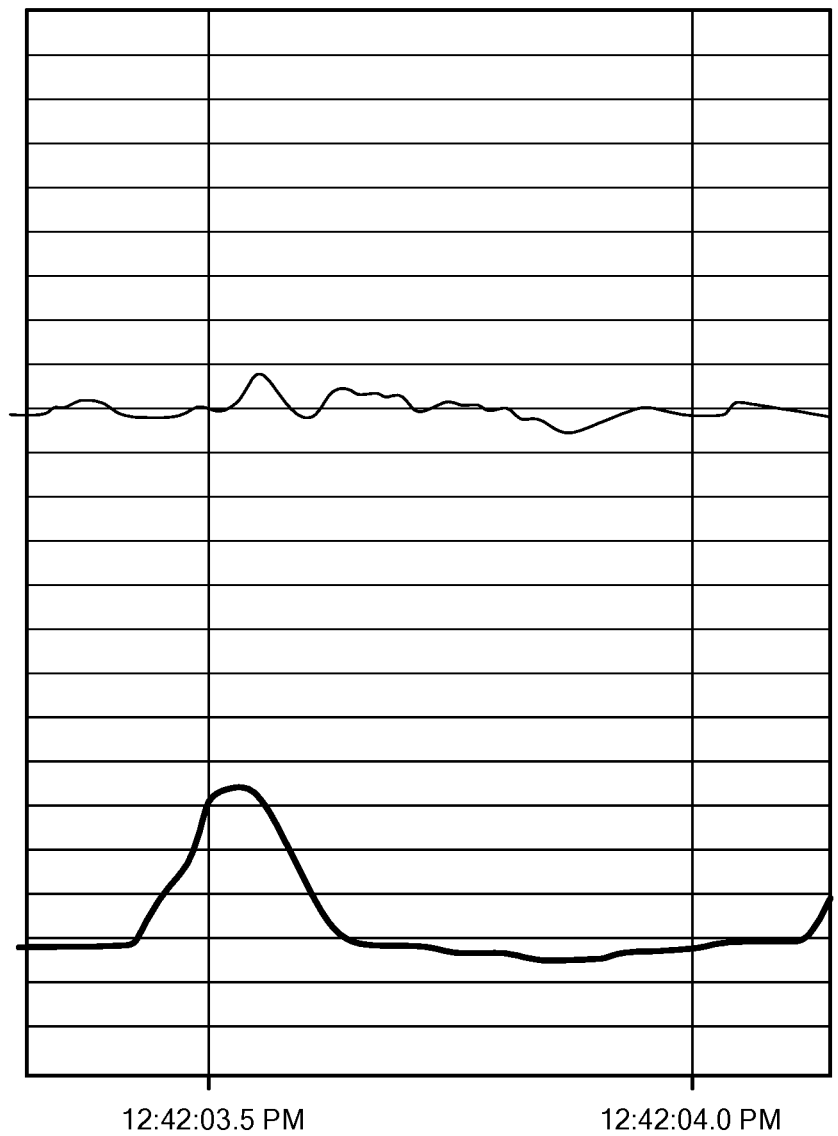
FIG. 13B is a graphical plot of left ventricular and aortic pressure of a patient using a blood pump operating at a speed of 2,800 RPM.

FIG. 13A further demonstrates the shrinking of the PCWI curve commensurate with the shrinking of the pressure-volume loop at an operational speed of 2,800 RPM. Now, the area of the PCWI curve is only about 77.5. As expected, in FIG. 13B, aortic valve closure persists at 2,800 RPM, as evidenced by the consistent difference between LVP and AOP.

Figure 14A:
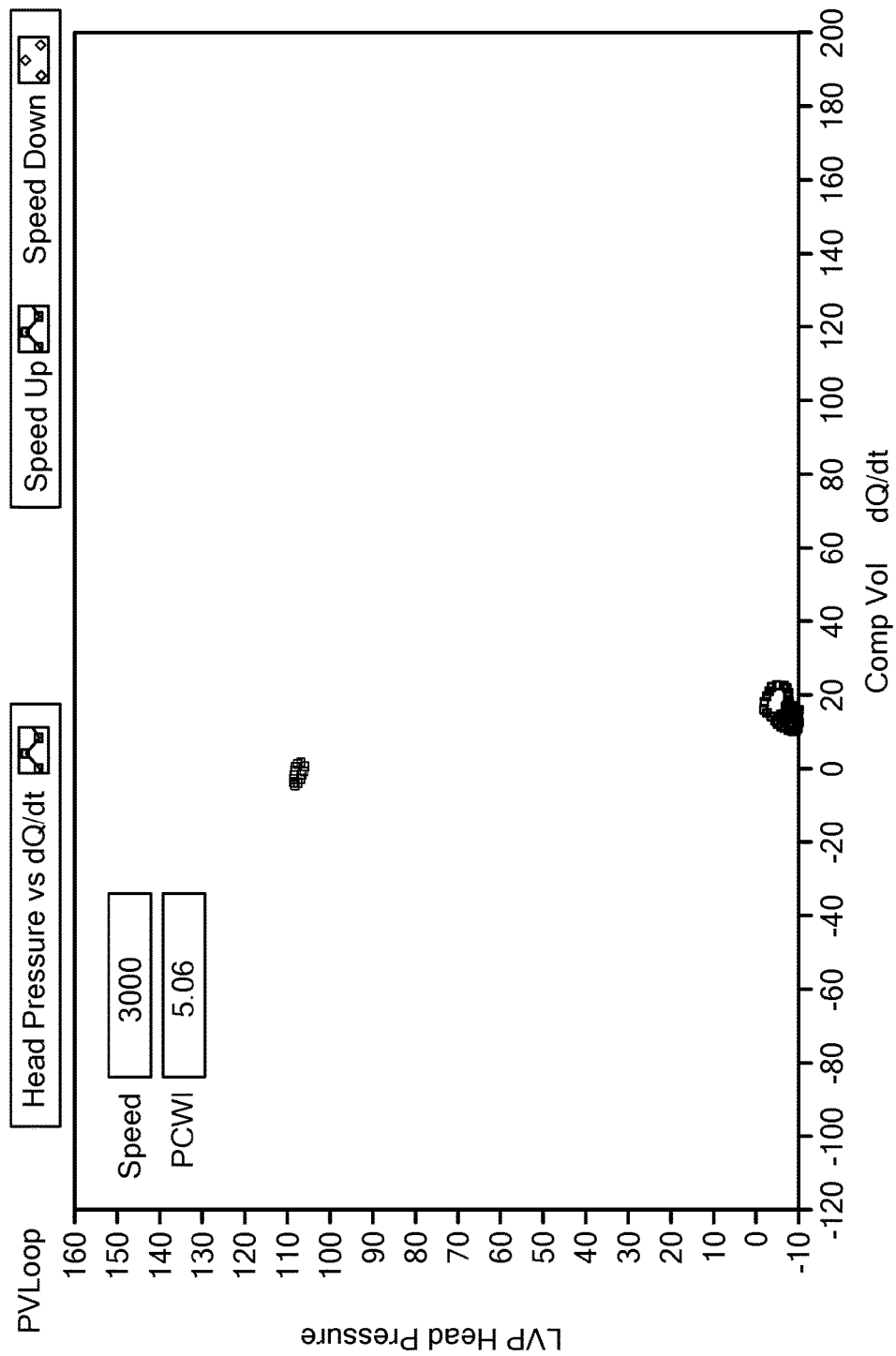
FIG. 14A, is a graphical plot of a measure of volume and a measure of pressure of a blood pump operating at a speed of 3,000 RPM.
Figure 14B:
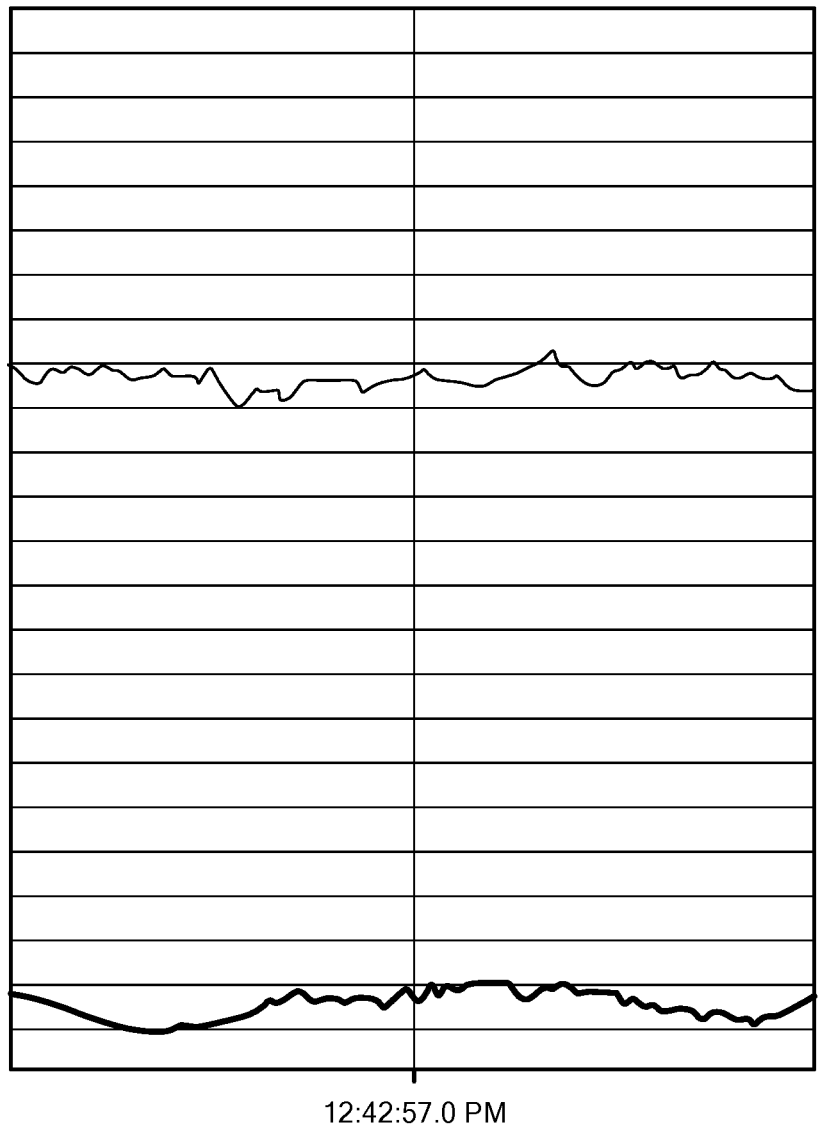
FIG. 14B is a graphical plot of left ventricular and aortic pressure of a patient using a blood pump operating at a speed of 3,000 RPM.

FIG. 14A demonstrates the even further shrinking of the PCWI curve, again commensurate with the shrinking of the pressure-volume loop, at an operational speed of 3,000 RPM. Now, the area of the PCWI curve is only about 5.06. As shown in FIG. 14B, not only does the aortic valve closure persist, but LVP and AOP remain relatively unchanged over the course of the cardiac cycle, since there is little change in either flow or pressure at any of the left ventricle, aorta, or pump.

In situations such as that of FIGS. 14A and 14B, there is little benefit to increasing the operating speed any further, since there is virtually no work left for the blood pump to perform. Even in situations such as that of FIGS. 11A and 11B, where increasing operating speed of the blood pump may result in aortic valve closure, it may also be undesirable to increase the operating speed. Even operation at a point before aortic valve closure may be undesirable for a given patient if the patient's heart is well enough to perform a given amount of work. Since PCWI values are a helpful way to characterize the amount of work performed by the patient's heart, and how much work remains for the pump to perform, the PCWI values may also be a helpful away to characterize a limit of desirable amount of pump work for a given patient.

The PCWI value may be used in several applications. For instance, the PCWI value may be compared to a predetermined value setting a limit. The limit may indicate a maximum amount of work for which it is desirable for the pump to perform, or for which partial-support status of the pump is maintained (e.g., preventing aortic valve closure). When the PCWI value is greater than the limit, a clinician may determine that it is safe or even desirable to increase the operating speed of the pump. However, when the PCWI value is less than the limit, the clinician may determine that it is undesirable or even unsafe to increase the operating speed. In such a case, if a patient complains of discomfort to the clinician, the clinician may at first glance wish to increase the pump speed, but after checking the patient's PCWI limit and the pumps' PCWI value, the clinician may determine that something else is wrong with the patient (e.g., cardiovascular accident, or other adverse cardiac event) for which increasing pump speed may not help, and may even hurt, the patient. Stated another way, if the clinician discovers from the PCWI value has passed a threshold limit indicative of a minimum amount of ventricular loading by the patient's heart, the clinician may conclude that the patient must be evaluated to determine the cause of reduced work performed by the patient's heart. Thus, the PCWI value may be used to detect aortic valve closures and/or adverse events at the patient's heart.

In some cases, the predetermined limit may be set on a patient-specific basis. Alternatively, the predetermined limit may vary on a condition-to-condition basis, and/or may be a standard figure applied for multiple patients.

In some cases, the predetermined limit may be stored in the memory of a control circuit (e.g., PCWI limit 235) and used to control operation of the pump. For instance, a given PCWI limit may be compared to a current PCWI value, and if the PCWI value is less than the PCWI limit, the control circuit may activate an alert and/or override any attempts to further increase operating speed of the pump, or may slow down the pump.

Another application of the PCWI value may be to detect an incipient suction condition. Specifically, a very low PCWI value (e.g., those shown in FIGS. 13A and 14A) indicate that there is little to no change of dQ/dt at the pump, nor is there much change in differential pressure. This may in turn be indicative that the ventricle of the patient's heart is not filling, and that suction on the ventricle is imminent. In those cases where a PCWI value indicative of such conditions is programmed into a control circuit, the control circuit may react to such a calculated PCWI by reducing an operational speed of the pump so as to allow the ventricle an opportunity to fill.

Another application of the PCWI value may be to detect blockages in the pump. For instance, if the pump is operating at a first speed, having a corresponding PCWI value, one would expect the PCWI to decrease with a corresponding increase in speed. However, if the operating speed of the pump is increased and the PCWI value remains unchanged, or if the PCWI value only changes by less than a threshold amount, it may indicate that the pump is not taking on work from the heart. This could be due to a blockage in the pump. Thus, the lack of change in the PCWI value is at least indicative of a greater likelihood of a blockage in the pump.

Yet another application of the PCWI value may be to detect a suction condition in a partial-support blood pump. For instance, if the pump is operating at a first speed, having a corresponding PCWI value, one would expect the PCWI to decrease with a corresponding increase in speed. However, under suction conditions, the flow rate of blood sharply drops towards zero at the beginning of diastole, and then sharply increases, causing a brief but large change in dQ/dt, and a brief but large change in differential pressure. This brief but large change may result in a PCWI curve enclosing a larger area than enclosed prior to suction, when the pump was operating under a condition of increasingly low flow pulsatility. Thus, if the operating speed of the pump is increased and the PCWI value actually increases (e.g., increases by any amount, increases by a threshold amount), it may indicate that the pump has caused a suction condition at the left ventricle of the patient. The operating speed of the pump may be reduced in response to this determination An even further application of the PWCI value may be to control a temporary transition of a full-assist blood pump to a partial-assist mode. In some cases, it is desirable to slow the operating speed of a full-assist blood pump so that the patient's heart forces open the aortic valve (or pulmonary valve) during systole. Even if the patient's heart is not healthy enough to be relied on to regularly pump blood, periodically opening the aortic valve may be beneficial to prevent disrepair of the valve itself (e.g., calcification, clotting, etc.). As explained above, the PCWI value may provide a good indication of whether the patient's heart is performing enough work to open the aortic valve. Thus, if a PCWI value corresponding to that amount of work is determined, that value may be used to ensure pump slowdown that causes aortic valve opening, or stated differently, that ensures AOP/LVP crossover, without having to rely on invasive measurements. If the PCWI value is stored in a memory of the pump control circuit, the control circuit may provide automated, intermittent slowdown of the pump (and then resumption of the previous operating speed) in order to temporarily open the patient's aortic valve.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended paragraphs.

What is claimed is:

1. A method of estimating an amount of work available to be performed by a blood pump implanted in a patient, comprising:

calculating a first coordinate value characterizing a volume of blood impelled in the pump and a second coordinate value characterizing a differential pressure across the pump for each of a plurality of flow rate data points of a given cardiac cycle of the patient, each flow rate data point indicative of a flow rate of blood through the pump;

determining an area enclosed by the first and second coordinate values of the plurality of flow rate data points, the determined area being indicative of an amount of work available to be performed by the blood pump;

determining a starting time of the given cardiac cycle based on the determined flow rate data points crossing a running average flow rate; and determining an ending time of the given cardiac cycle based on the determined flow rate data points crossing the running average flow rate;

the plurality of flow rate data points of the given cardiac cycle being indicative of a flow rate of blood between the starting time and the ending time.

2. The method of claim 1, wherein determining the starting and ending times are further based on one of:

identifying consecutive instances of the determined flow rate data points crossing the running average flow rate with a negative slope;

identifying consecutive instances of the determined flow rate data points crossing the running average flow rate with a positive slope; and identifying three consecutive instances of the determined flow rate data points crossing of the running average flow rate, the first of the three consecutive instances being the starting time and the third of the three consecutive instances being the ending time.

3. The method of claim 1, wherein for each of the flow rate data points of the given cardiac cycle of the patient, the calculated first coordinate value is a derivative of the flow rate data point.

4. The method of claim 1, wherein for each of the flow rate data points of the given cardiac cycle of the patient, the calculated second coordinate value is a differential pressure corresponding to the flow rate data point.

5. The method of claim 4, further comprising determining a rotational speed of the blood pump, wherein the second coordinate value is determined at least in part using the determined rotational speed of the blood pump.

6. The method of claim 4, wherein the calculated second coordinate value is interpolated from a reference curve correlating differential pressure across the pump and flow rate through the pump for a given rotational speed of the blood pump.

7. The method of claim 1, wherein the flow rate data points are determined based on a non-invasive estimation of flow rate.

8. The method of claim 1, further including comparing the determined area to a predetermined value indicative of a minimum allowable amount of ventricular loading, wherein the determined area being less than the predetermined value is indicative of the presence of adverse condition.

* * * * *

UNITED STATES PATENT AND TRADEMARK OFFICE
CERTIFICATE OF CORRECTION

PATENT NO. : 10,159,775 B2
APPLICATION NO. : 15/424057
DATED : December 25, 2018
INVENTOR(S) : Neil Voskoboynikov and Pedro Grave De Peralta It is certified that error appears in the above-identified patent and that said Letters Patent is hereby corrected as shown below:

In the Claims

Please replace Claim 8, Column 2, Line 66 which presently states "is indicative of the presence of adverse condition", with the following:
--is indicative of the presence of an adverse condition--

Signed and Sealed this
Sixteenth Day of April, 2019

Andrei Iancu
*Director of the United States Patent and Trademark Office*